US009517254B2

(12) United States Patent
Sitchon et al.

(10) Patent No.: US 9,517,254 B2
(45) Date of Patent: Dec. 13, 2016

(54) TREATMENT REGIMENS

(71) Applicant: S1 Biopharma, Inc., Jersey City, NJ (US)

(72) Inventors: Nicolas G. Sitchon, Jersey City, NJ (US); Robert E. Pyke, New Fairfield, CT (US); John F. Kaufmann, Beltsville, MD (US)

(73) Assignee: S1 BIOPHARMA, INC., Jersey City, NJ (US)

( * ) Notice: Subject to any disclaimer, the term of this patent is extended or adjusted under 35 U.S.C. 154(b) by 0 days.

(21) Appl. No.: 14/420,112

(22) PCT Filed: Aug. 6, 2013

(86) PCT No.: PCT/US2013/053843
§ 371 (c)(1),
(2) Date: Feb. 6, 2015

(87) PCT Pub. No.: WO2014/025814
PCT Pub. Date: Feb. 13, 2014

(65) Prior Publication Data
US 2015/0150946 A1    Jun. 4, 2015

Related U.S. Application Data

(60) Provisional application No. 61/679,999, filed on Aug. 6, 2012.

(51) Int. Cl.
| | | |
|---|---|---|
| A61K 38/22 | (2006.01) |
| A61K 31/496 | (2006.01) |
| A61K 31/137 | (2006.01) |
| A61K 45/06 | (2006.01) |
| A61K 38/11 | (2006.01) |

(52) U.S. Cl.
CPC ............ *A61K 38/22* (2013.01); *A61K 31/137* (2013.01); *A61K 31/496* (2013.01); *A61K 38/11* (2013.01); *A61K 45/06* (2013.01)

(58) Field of Classification Search
None
See application file for complete search history.

(56) References Cited

U.S. PATENT DOCUMENTS

| | | |
|---|---|---|
| 4,687,771 A | 8/1987 | Gamble et al. |
| 6,337,328 B1 | 1/2002 | Fang et al. |
| 2005/0245539 A1 | 11/2005 | Mendla et al. |
| 2006/0154908 A1 | 7/2006 | Patel et al. |
| 2006/0211685 A1 | 9/2006 | Pyke et al. |
| 2011/0105519 A1 | 5/2011 | Mendla et al. |
| 2012/0172304 A1 | 7/2012 | Leonard et al. |

FOREIGN PATENT DOCUMENTS

| | | |
|---|---|---|
| CN | 1946404 A | 4/2007 |
| DE | 4321965 A1 | 1/1995 |
| JP | 2002322085 A | 11/2002 |
| WO | WO-2004030524 A2 | 4/2004 |
| WO | WO-2004078147 A2 | 9/2004 |
| WO | WO-2005102342 A1 | 11/2005 |
| WO | WO-2006055854 A2 | 5/2006 |
| WO | WO-2006096435 A1 | 9/2006 |
| WO | WO-2008075162 A2 | 6/2008 |
| WO | WO-2011140608 A1 | 11/2011 |
| WO | WO-2011146726 A1 | 11/2011 |
| WO | WO-2012016229 A2 | 2/2012 |
| WO | WO-2012138653 A2 | 10/2012 |

OTHER PUBLICATIONS

Bancroft. J Endrocrinology. 186, 411-427 (2005).*
Clayton. Primary Psychiatry. 10(1), 55-61 (2003).*
Clark et al. Add Pharmacother. 34, 1007-1012 (2000).*
International Search Report for PCT/US2013/053843 Dated Dec. 20, 2013.
Werneke, U. et al.; "Antidepressants and Sexual Dysfunction", Acta Psychiatrica Scandinavica, 2006, Vo. 114, pp. 384-307.
Seagraves, R.T., et al.; "Bupropion Sustained Release (SR) for the Treatment of Hypoactive Sexual Desire Disorder (HSDD) in Nondepressed Women"; Journal of Sex & Marital Therapy, 2001. vol. 27, pp. 303-316.
Lance, R. et al; "Oral Trazodone as Empirical Therapy for Erectile Dysfunction: A Retrospective Review"; Urology, 1995, vol. 46, pp. 117-120.
D'Aquila, P., et al; "Anti-anhedonic Actions of the Novel Serotonergic Agent Flibanserin, a Potential Rapidly-Acting Antidepressant"; European Journal of Pharmacology, 1997, vol. 340, pp. 121-132.
American Psychiatric Association, "Sexual and Gender Identity Disorders", Diagnostic and Statistical Manual of Mental Disorders, 4th Edition, 1994, pp. 493-522.
Anderson-Hunt et al., Increased female sexual response after oxytocin. BMJ. Oct. 8, 1994;309(6959):929.
Basson et al., Summary of the recommendations on sexual dysfunctions in women. J Sex Med. Jan. 2010;7(1 Pt 2):314-26.
Berge et al., Pharmaceutical Salts. J. Pharm. Sci. Jan. 1977; 66(1):1-19.
Brotto et al., Women's sexual desire and arousal disorders. J Sex Med. Jan. 2010;7(1 Pt 2):586-614.
Burri et al., The acute effects of intranasal oxytocin administration on endocrine and sexual function in males. Psychoneuroendocrinology. Jun. 2008;33(5):591-600.
Chadman et al., New directions in the treatment of autism spectrum disorders from animal model research. Expert Opinion on Drug Discovery. vol. 7, No. 5, 2012. pp. 407-416.
Chinese Office Action for Chinese Application No. 201280027260.7, dated Dec. 22, 2014.
Chinese Office Action for Chinese Application No. 201280027260.7, dated Nov. 2, 2015.
Chinese Office Action for Chinese Application No. 201380052215.1, dated May 5, 2016.
Clayton et al., Standards for clinical trials in sexual dysfunction in women: research designs and outcomes assessment. J Sex Med. Jan. 2010;7(1 Pt 2):541-60.
Craven et al., What are the Altenatives to Nefazodone? Canadian Psychiatric Association Bulletin, 2004;36(4):21.
Derogatis et al., Characterization of hypoactive sexual desire disorder (HSDD) in men. J Sex Med. Mar. 2012;9(3):812-20.

(Continued)

*Primary Examiner* — Amber D Steele
*Assistant Examiner* — Schuyler Milton
(74) *Attorney, Agent, or Firm* — Mintz Levin Cohn Ferris Glovsky and Popeo, P.C.

(57) ABSTRACT

The invention further relates to compounds, pharmaceutical compositions and methods for treating all disorders of human sexual function including hypoactive sexual desire disorder (HSDD) in a subject.

20 Claims, No Drawings

(56) References Cited

OTHER PUBLICATIONS

Eurasian Office Action for Eurasian Application No. 201391459, dated Apr. 2, 2015.
European Office Action for European Application No. 12768489.2, dated Feb. 1, 2016.
European Search Report for European Application No. 12768489.2, dated Jul. 21, 2014.
European Search Report for European Application No. 13827390.9, dated Jan. 29, 2016.
European Search Report for European Application No. 13827390.9, dated Apr. 22, 2016.
Fink et al., Trazodone for erectile dysfunction: a systematic review and meta-analysis. BJU Int. Sep. 2003;92(4):441-6.
Fooladi et al., An update on the pharmacological management of female sexual dysfunction. Expert Opin Pharmacother. Oct. 2012;13(15):2131-42.
Ghanbari et al., Sustained administration of trazodone enhances serotonergic neurotransmission: in vivo electrophysiological study in the rat brain. J Pharmacol Exp Ther. Oct. 2010;335(1):197-206.
Hatzichristou et al., Recommendations for the clinical evaluation of men and women with sexual dysfunction. J Sex Med. Jan. 2010;7(1 Pt 2):337-48.
Herrera-Guzmán et al., Cognitive predictors of treatment response to bupropion and cognitive effects of bupropion in patients with major depressive disorder. Psychiatry Res. Jul. 15, 2008;160(1):72-82.
International Search Report for PCT/US2012/031991, dated Oct. 12, 2012.
Ishak et al., Male anorgasmia treated with oxytocin. J Sex Med. Apr. 2008;5(4):1022-4.
Japanese Office Action for Japanese Application No. 2014-503910, dated Feb. 9, 2016.
Kirsch et al., Oxytocin modulates neural circuitry for social cognition and fear in humans. J Neurosci. Dec. 7, 2005;25(49):11489-93.
Laumann et al., Sexual dysfunction in the United States: prevalence and predictors. JAMA. Feb. 10, 1999;281(6):537-44.
MacDonald et al., A review of safety, side-effects and subjective reactions to intranasal oxytocin in human research. Psychoneuroendocrinology. Sep. 2011;36(8):1114-26.
MacDonald et al., Dramatic improvement in sexual function induced by intranasal oxytocin. J Sex Med. May 2012;9(5):1407-10.
Mexican Office Action for Mexican Application No. MX/a/2013/011623, dated Mar. 1, 2016.
Modell et al., Effect of bupropion-SR on orgasmic dysfunction in nondepressed subjects: a pilot study. J Sex Marital Ther. Jul.-Sep. 2000;26(3):231-40.
Monleón et al., Antidepressant drugs and memory: insights from animal studies. Eur Neuropsychopharmacol. Apr. 2008;18(4):235-48.
Nierenberg et al., Trazodone for antidepressant-associated insomnia. Am J Psychiatry. Jul. 1994;151(7):1069-72.
Peterson et al., Anxiety and sexual stress in men and women undergoing infertility treatment. Fertil Steril. Oct. 2007;88(4):911-4.
Rowland et al., Bupropion and sexual function: a placebo-controlled prospective study on diabetic men with erectile dysfunction. J Clin Psychopharmacol. Oct. 1997;17(5):350-7.
Scandroglio et al., Ex vivo binding of flibanserin to serotonin 5-HT1A and 5-HT2A receptors. Pharmacol Res. Feb. 2001;43(2):179-83.
Schenck et al., Combined bupropion-levodopa-trazodone therapy of sleep-related eating and sleep disruption in two adults with chemical dependency. Sleep. Aug. 1, 2000;23(5):587-8.
Search Report for Singapore Application No. 2013074083, dated Sep. 5, 2014.
Shifren et al., Sexual problems and distress in United States women: prevalence and correlates. Obstet Gynecol. Nov. 2008;112(5):970-8.
Stryjer et al., Trazodone for the treatment of sexual dysfunction induced by serotonin reuptake inhibitors: a preliminary open-label study. Clin Neuropharmacol. Mar.-Apr. 2009;32(2):82-4.
Tordjman. Treatment of Inhibition of Sexual Desire in Women by Trazodone. Contraception Fertilite Sexualite. 1986; 14(10): 935-939.
Written Opinion for Singapore Application No. 11201500919P, dated Feb. 16, 2016.
Written Opinion for Singapore Application No. 2013074083, dated Feb. 22, 2016.
Written Opinion for Singapore Application No. 2013074083, dated May 21, 2015.
Written Opinion for Singapore Application No. 2013074083, dated Oct. 3, 2014.
Zourkova et al., The Efficacy of Bupropion and Trazodone in the Treatment of Hypoactive Sexual Desire Disorder and Orgasm Dysfunction in Non-Depressed Women. Ceska A Slovenska Psychiatrie. 2008; 104(2): 1068.
American Psychiatric Association, Diagnostic and Statistical Manual of Mental Disorders, 5th Edition, 2013, pp. 423-450.
Eurasian Office Action for Eurasian Application No. 201590349, dated Jun. 20, 2016.
Harrison et al., Harrison's Principles of Internal Medicine, 13th Edition, McGraw-Hill, 1994, pp. 267-268, 2407-2408, 2459.
Lough, W.J. Chiral Liquid Chromatography, Chapman and Hall, 1989, pp. 14-35.
The Physicians' Desk Reference, 50th Edition, 1997, pp. 308, 316, 503-505, 1204-1207, 2679.
Australian Examination Report for Application No. 2012240388, dated Jun. 6, 2016.
Wikipedia, "Diagnostic and Statistical Manual of Mental Disorders," Wikipedia.org. <https://en.wikipedia.org/wiki/Diagnostic_and_Statistical_Manual_of_Mental_Disorders>.
European Neuropsychopharmacology: The Journal of the European College of Neuropsychopharmacology, V. 19, Suppl. 3, S362. Papers of the 22nd ECNP Congress. Sep. 12-16, 2009, Istanbul, Turkey.
Office Action for Israeli Application No. 228729, dated Aug. 14, 2016. [English translation and original].
Office Action for Japanese Application No. 2014-503910, dated Oct. 4, 2016. [English translation and original].

\* cited by examiner

TREATMENT REGIMENS

CROSS REFERENCE TO RELATED APPLICATIONS

This application is the national phase under 35 U.S.C. §371 of PCT International Application No, PCT/US2013/053843, filed Aug. 6, 2013, which claims the benefit of U.S. Provisional Application No. 61/679,999 filed on Aug. 6, 2012, the entire disclosures of which is are hereby incorporated in its entirety.

BACKGROUND OF THE INVENTION

Sexual Dysfunction (SD) is described as a disorder of or an interruption in sexual functioning. In women, the most common type of sexual disorder is generalized, acquired HSDD defined by the Diagnostic and Statistical Manual, $4^{th}$ Edition, Text Revision (American Psychiatric Association, 2000; DSM-IV-TR) as: "The persistent lack (or absence) of sexual fantasies or desire for any form of sexual activity marked by distress or interpersonal difficulty and not better accounted for by another disorder (except another sexual dysfunction) direct physiological effects of a substance (including medications) or a general medical condition." The presence of distress or interpersonal difficulty is an integral part of sexual disorders and is central to the diagnosis of the condition. Approximately 1 in 10 women reported low sexual desire with associated distress, which may be HSDD.

Synonyms for HSDD include sexual aversion, i.e., extreme aversion to, absence of, and avoidance of all, or almost all, sexual contact with a partner; inhibited sexual desire; sexual apathy; loss of libido; decreased sexual desire; distressing loss of sexual desire; and sexual anorexia. HSDD occurs in both sexes. It is considered to be the most common of all female sexual disorders, possibly occurring in as many as 10% of women in the United States.

In women, a majority of HSDD cases are generalized in subtype, though a substantial minority of cases may relate to dissatisfaction or loss of interest in the sexual partner. Either subtype of HSDD can lead to general feelings of dissatisfaction in the person and/or discord in their personal relationships, including for example marital discord. Sexual disorders, whether generalized or situational, often do not respond to counseling therapy, and frequently culminate in separation, finding a new sexual partner, and divorce.

The other phases of sexual function, sexual arousal and orgasm, are also subject to impairment. In women, dysfunctions in these sexual phases, if sufficiently distressing, are known, respectively, as Female Sexual Arousal Disorder (FSAD) and Female Orgasmic Disorder (FOD) in DSM-IV-TR. Collectively, they impair sexual function in almost as many women as does HSDD (Shifren J L et al, Sexual problems and distress in United States women: prevalence and correlates. Obstet Gynecol. 2008 November; 112(5): 970-81. Women in the peri- and post-menopause are the most affected subpopulation with such problems. In the US, in the age group 45-64 years, the prevalence of FSAD is about 3.1 million; of FOD, 2.4 million. Little overlap of these disorders was found in the largest, most representative survey of women's sexual function (the PRESIDE study, Shifren et al, ibid.), so the overall number of US women affected with FSAD or FOD is over 5 million.

In men, dysfunction in arousal (in erection) is well recognized; dysfunctional delay in, or absence of, orgasm (ejaculation) also occurs with some frequency. If it causes significant sexual distress, the disorder is called Male Orgasmic Disorder (MOD; delayed ejaculation). Male dysfunctionally premature ejaculation (PE) is much more frequent than any of these problems, occurring in up to 30% of younger men (Laumann et al., Sexual dysfunction in the United States: Prevalence and predictors, JAMA, 1999; 281:537-44).

Sexual dysfunction may also be manifested as a significant burden in the course of physical diseases. Sexual dysfunction is frequent in women with chronic, fatiguing medical illness, especially Female HSDD or FSAD due to breast cancer, diabetes mellitus, or irritable bowel syndrome or due to combined factors including one of these medical diseases. These conditions occur mainly in middle-aged to older patients. Collectively, these conditions cause sexual dysfunction, mainly desire disorder, in over 7.8 million women age 45-64 in the US (breast or gynecologic cancer, 1.5 million; diabetes, at least 3.4 million; irritable bowel, at least 2.9 million). SD in Men with chronic diseases is little studied but can be presumed from the ample evidence on women to be another large set of clinically and epidemiologically significant health problems. The most authoritative arbiter of diagnostic names and criteria on sexual dysfunction, the DSM-IV-TR, recognizes eight kinds of sexual disorders due to chronic physical disease: Sexual Dysfunction due to General Medical Conditions (e.g., irritable bowel syndrome, diabetes, cancer); Female HSDD due to General Medical Conditions (e.g., irritable bowel syndrome, diabetes, cancer); Male HSDD due to General Medical Conditions (e.g., irritable bowel syndrome, diabetes, cancer); Male Erectile Disorder due to General Medical Conditions (e.g., irritable bowel syndrome, diabetes, cancer); Female Dyspareunia due to General Medical Conditions (e.g., irritable bowel syndrome, diabetes, cancer); Male Dyspareunia due to General Medical Conditions (e.g., irritable bowel syndrome, diabetes, cancer); Other Female Sexual Dysfunction due to General Medical Conditions (e.g., irritable bowel syndrome, diabetes, cancer) if some other feature is predominant (e.g., Orgasmic Disorder) or no feature predominates; and Other Male Sexual Dysfunction due to General Medical Conditions (e.g., irritable bowel syndrome, diabetes, cancer) if some other feature is predominant (e.g., Orgasmic Disorder) or no feature predominates.

Collectively, in this document, all of the sexual dysfunctions and disorders described above are called sexual dysfunctions, sexual disorders, or SD.

As there is no currently approved treatment for HSDD or any other sexual disorder except (male) erectile dysfunction in the United States, a therapeutic composition and methods for ameliorating sexual disorders is an unmet need for a significant portion of the population and their quality of life. Delineated herein are compositions and methods of treatment that may be useful to address this unmet need based on heretofore unexpected properties possessed by the subject compositions.

Erectile Dysfunction (ED) is the only male sexual dysfunction for which pharmacotherapies are broadly available. Sexual disorders other than ED, e.g., HSDD, are also common in men, although research on non-ED male sexual disorders has lagged compared to that in women. However, the cross-national US survey published in 1999 by Laumann et al. showed that male lack of interest in sex, at 15% of men aged 18-59, was about as frequent as erectile dysfunction (18%). In March (Derogatis et al, J Sex Med 2012; 9:812-820), a research group applied a battery of validated scales to men with HSDD vs. those with no sexual dysfunction.

The men with HSDD had dramatic impairments on all rating scales relating to HSDD: on the Sexual Concerns Index-Male, a measure of male sexual distress; the UCLA Psychosexual Diary's measure of sexual activity; and the Male Desire Scale, a measure of sexual desire; but did not have ED: [International Index of Erectile Function (IIEF)-5 median score] or depression [Beck Depression scale] or low testosterone: men with low or low-normal testosterone levels (<300 ng/dL) were excluded. Their data show that male HSDD is a real problem of clinical magnitude. *$p<0.0001$ for each variable; sample sizes were about 100

No pharmacologic treatment is available in most countries including the US for either men or women with sexual disorders other than for men with ED, although a testosterone transdermal system was approved for women with postmenopausal HSDD in Europe in 2005.

Yet another male sexual dysfunction is frequent, though not the subject of a DSM-IV-TR diagnosis: Male sexual performance anxiety was a problem for 17% of US men age 18-59 in the cross-national survey published by Laumann in 1999 in JAMA, about the same incidence as for erectile dysfunction (ED) and male lack of sexual interest. Male sexual performance anxiety was about twice as prevalent as ED in US men under age 50. It is little studied but can cause significant distress, especially in male patients in infertility clinics. Peterson B D, Newton C R, and Feingold T. in "Anxiety and sexual stress in men and women undergoing infertility treatment," in Fertility and Sterility 2007 October; 88(4):911-4, Epub 2007 Apr. 11, found in a prospective study at a University-affiliated teaching hospital for in vitro fertilization and intrauterine insemination (306 women, 295 men) a strong linkage between anxiety and sexual stress in men and concluded that sexual stress among infertile men may be more closely tied to performance anxiety rather than to a more general deterioration in sexual satisfaction associated with infertility.

Male sexual performance anxiety, while not a disorder recognized in DSM-IV-TR or ICD-10, is recognized as a necessary focus in the recommended clinical evaluation of men with sexual dysfunction according to the Third International Consultation on Sexual Medicine (Paris, July 2009). Hatzichristou D, Rosen R C, Derogatis L R, et al, Recommendations for the Clinical Evaluation of Men and Women with Sexual Dysfunction, J Sex Med 2010; 7:337-348. These experts recommend diagnostic workup for male sexual performance anxiety because it may cause or result from the recognized male sexual disorders such as ED (psychogenic impotence) and premature ejaculation.

The model of sexual functioning that is most accepted is one in which sexual desire leads to arousal, and eventually orgasm. Even E D, currently the most treatable of sexual dysfunctions, is unlikely to be aided by pharmacotherapy unless desire can be restored. Thus, loss of desire is of primary concern for treating all disorders of sexual function.

The current invention relates to combinations of a $5\text{-HT}_{1A}$ receptor agonist and/or $5\text{-HT}_{2A}$ receptor antagonist (e.g., trazodone, nefazodone, mirtazapine, flibanserin), a norepinephrine-dopamine reuptake inhibitor (e.g., bupropion), and/or an oxytocin receptor (OXTR) agonist (e.g., carbetocin, oxytocin, Syntocinon®) and their use to augment sexual desire, arousal, and orgasm. Their ability to help men feel desire will also aid male sexual performance anxiety. These combinations will be particularly effective for each of these disorders in men and women because they will allow the corrective effects of the individual agents to become manifest without being masked by the side effects of either drug, and in particular it will allow rapid relief of symptoms because the effective dose can be given immediately due to the low expected side effects, instead of requiring weeks of up-titration to overcome side effects over time. This makes Lorexys®, a fixed combination of bupropion and trazodone, of special value for male HSDD and sexual performance anxiety as disorders that cause distress and disrupt quality of life on the days when a man is to have sex with a partner.

The current invention relates to combinations of a $5\text{-HT}_{1A}$ receptor agonist and/or $5\text{-HT}_{2A}$ receptor antagonist (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), a norepinephrine-dopamine reuptake inhibitor (e.g., bupropion), and/or an oxytocin receptor (OXTR) agonist (e.g., carbetocin, oxytocin, Syntocinon®) and their use to augment sexual desire, arousal, and orgasm. Their ability to help men feel desire will also aid male sexual performance anxiety. These combinations will be particularly effective for each of these disorders in men and women because they will allow the corrective effects of the individual agents to become manifest without being masked by the side effects of either drug, and in particular it will allow rapid relief of symptoms because the effective dose can be given immediately due to the low expected side effects, instead of requiring weeks of up-titration to overcome side effects over time. This makes Lorexys®, a fixed combination of bupropion and trazodone, of special value for male HSDD and sexual performance anxiety as disorders that cause distress and disrupt quality of life on the days when a man is to have sex with a partner.

The current invention also relates to combinations of a $5\text{-HT}_{1A}$ receptor agonist and/or $5\text{-HT}_{2A}$ receptor antagonist (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), and/or a $5\text{-HT}_{2C}$ receptor antagonist, and/or a 5HT-2c receptor agonist, (e.g., lorcaserin, vabicaserin, PRX-00933, YM348, and metachlorophenylpiperazine, mCPP), a norepinephrine-dopamine reuptake inhibitor (e.g., bupropion), and/or other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and/or an oxytocin receptor (OXTR) agonist (e.g., carbetocin, oxytocin, Syntocinon®) and their use to augment sexual desire, arousal, and orgasm. Their ability to help men feel desire will also aid male sexual performance anxiety. These combinations will be particularly effective for each of these disorders in men and women because they will allow the corrective effects of the individual agents to become manifest without being masked by the side effects of either drug, and in particular it will allow rapid relief of symptoms because the effective dose can be given immediately due to the low expected side effects, instead of requiring weeks of up-titration to overcome side effects over time. This makes Lorexys®, a fixed combination of bupropion and trazodone, of special value for male HSDD and sexual performance anxiety as disorders that cause distress and disrupt quality of life on the days when a man is to have sex with a partner.

Disorders of cognition are also frequent, and are of particular concern because of their high prevalence in older patients (an enlarging segment of the population), the disability they cause, and their intractability to current treatments. Improvement in cognition as augmentation of cognition for therapeutic purposes is also of interest, e.g., in the circumstances of subjects whose cognitive skills are limiting for tasks that require learning or vigilance. The invention provides a method of treating a subject suffering from or susceptible to a cognitive disorder or otherwise in need of improvement in cognition with a composition comprising a 5-HT$_{1A}$ agonist, a 5-HT$_{2A}$ antagonist, a norepinephrine-dopamine reuptake inhibitor, an oxytocin receptor (OXTR) agonist, and a pharmaceutically acceptable carrier.

Depressive disorders are also frequent (lifetime risk in women, 10-25%; in men, 5-12%) and are of particular concern because of the disability they cause, the high likelihood of failure with initial treatment (only about 50% of patients with Major Depressive Disorder respond to any one antidepressant, the high frequency of incomplete response to currently available treatments (only about 30% of patients achieve full remission with a given antidepressant), their increasing frequency of treatment-resistance, and especially because they often lead to suicide, in about 15% of patients (DSM-IV-TR). The invention provides a method of treating a subject suffering from or susceptible to a depressive disorder comprising administering to a subject in need thereof a therapeutically effective amount of a composition comprising a 5-HT$_{1A}$ agonist, a 5-HT$_{2A}$ antagonist, a norepinephrine-dopamine reuptake inhibitor, an oxytocin receptor (OXTR) agonist, and a pharmaceutically acceptable carrier.

It is not readily apparent from published literature reports that oxytocin (OT) can relieve human sexual dysfunction. Though a case report of pro-sexual effects of transnasal OT has been published for each of three very different patients [a postpartum woman without sexual dysfunction: Anderson-Hunt and Dennerstein, Brit Med J. 1994; 309:929; an elderly man with orgasmic disorder: IsHak et al., J Sex Med. 2008; 5:1022-4, and a complex psychiatric patient without sexual dysfunction: MacDonald and Feifel, J Sex Med 2012; 9:1407-1410], the only published placebo-controlled study showed no significant advantage for oxytocin: 24 International Units (IU) of intranasal OT failed to increase arousal or orgasm in men on the primary outcome scale, the "Acute Sexual Experiences Scale (ASES)." The authors concluded that "the effects of OT on sexual behavior were equivocal . . . " [Burri et al, Psychoneuroendocrinology. 2008; 33:591-600.] Also, in the most recent review of the side effects of transnasal OT, in which almost a thousand subjects were treated with OT (Syntocinon®) in almost all studies) in controlled studies to investigate non-sexual effects, no events of any type of increase in sexual function were reported [MacDonald et al, Psychoneuroendocrinology. 2011 September; 36(8):1114-26].

However, OT mediates pro-social and anti-anxiety effects, doing so through effects on the amygdala in a placebo-controlled study. [Kirsch et al., J. Neuroscience 2005; 25(49):11489-11493]. It is a novel aspect of the invention that these properties will specifically aid all DSM-IV-TR-recognized sexual dysfunction disorders listed as having the DSM-IV-TR subtype "due to situational factors," i.e., in men or women who are in a relationship in which sexual activity has deteriorated in frequency and/or satisfaction because of increasing loss of trust and/or anxiety about performance, avoidance patterns etc., that occur as a consequence of any of the recognized sexual dysfunction disorders: in the male partner, HSDD, ED, PE, MOD, and dyspareunia, and in (the epidemiologically frequent but not DSM-IV-recognized condition of) male sexual performance anxiety; in the female partner, HSDD, FSAD, FOD, and dyspareunia. It is a novel aspect of the invention that the same properties of oxytocin, aiding trust and reducing social anxiety, will aid most of the other subtypes of each of these disorders of sexual function, i.e., the subtypes "due to psychological factors and "due to combined factors." "Situational" is defined in DSM-IV-TR as applying "if the sexual dysfunction is limited to certain types of stimulation, situations, or partners," which is the opposite of the Generalized type. "Due to Psychological Factors" applies "when psychological factors are judged to have the major role in the onset, severity, exacerbation, or maintenance of the Sexual Dysfunction . . . . " "Due to Combined Factors" is defined as applying "when psychological factors are judged to have a role in the onset, severity, exacerbation, or maintenance of the Sexual Dysfunction . . . . "

It is a novel aspect of the invention that oxytocin is useful to treat the aforementioned subtypes of every diagnostic category of sexual dysfunction. Drawing on clinical experience in couples having a long-term partnered relationship, sexual dysfunction in one partner ordinarily worsens because of the other partner's reaction over time to that sexual dysfunction, and can cause sexual dysfunction in the partner, too. For example, generalized HSDD in a woman is likely to lead her to non-receptivity, which may lead her to a psychosocially destructive pattern of avoidance behavior regarding potential sexual situations. The male partner learns to avoid sexual frustration, anger, arguments etc. by also practicing avoidance behavior. At first this may simply be sublimation, but the likely result over time is atrophy of all sexual aspects of the union, including sexual dysfunction in the male partner—performance anxiety likely occurring first, then HSDD, ED, and/or PE. That leads to further decline in the sexual relationship. The woman's HSDD was originally, and logically remains, generalized. But both partners' sexual disorders may then alternatively be subtyped as situational, due to psychological factors, or due to combined factors.

Similarly, it is another aspect of the invention that oxytocin specifically aids all additionally proposed DSM-5 sexual dysfunction disorders (Male HSDD, Erectile Disorder, Delayed Ejaculation, Female Sexual Interest/Arousal Disorder, Genito-Pelvic Pain/Penetration Disorder, Substance/Medication-Induced Sexual Dysfunction, and Sexual Dysfunction Not Elsewhere Classified) with the proposed Specifiers of Situational, Partner factors (e.g., partner's sexual problems, partner's health status), and Relationship factors (e.g., poor communication, discrepancies in desire for sexual activity). [www.dsm5.org, Aug. 2, 2012].

The current invention relates to combinations of a 5-HT$_{1A}$ receptor agonist, 5-HT$_{2A}$ receptor antagonist, 5-HT$_{2C}$ receptor antagonist, or combinations thereof (e.g., trazodone). The current invention also relates to combinations of a 5-HT$_{1A}$ receptor agonist, 5-HT$_{2A}$ receptor antagonist, 5-HT$_{2C}$ receptor antagonist, or combinations thereof (e.g., trazodone), and a norepinephrine-dopamine reuptake inhibitor (e.g. bupropion), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. The current invention also relates to combinations of a 5-HT$_{1A}$ receptor agonist, 5-HT$_{2A}$ receptor antagonist (e.g., trazodone, nefazodone, mirtazapine, flibanserin), a norepinephrine-dopamine reuptake inhibitor (e.g. bupropion), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. These combinations are particularly effective for each of these disorders as they allow the corrective effects of the individual agents to become manifest without being masked by the side effects of either drug, and in particular it allow rapid relief of symptoms because the effective dose can be given immediately due to the low expected side effects, instead of requiring weeks of up-titration to overcome side effects over time. Reduced toxicity is provided by a compound of the invention when administered in vivo, e.g., formulating bupropion, by itself a mild stimulant, with trazodone, by itself a moderate sedative, in the proprietary ratio of Lorexys, will neutralize the main side effects of each of the two drugs. This makes Lorexys®, a fixed combination of bupropion and trazodone, of special value for treating acute symptoms such as suicidality, disabling symptoms such as inability to work or otherwise function, especially for older patients who generally are more prone to side effects and for whom adverse effects cause more risk, and especially because such a combination can be prescribed by a health provider with less specialized expertise in pharmacologic treatment of neuro-psychiatric disorders.

The current invention relates to combinations of a 5-$HT_{1A}$ receptor agonist, 5-$HT_{2A}$ receptor antagonist, 5-$HT_{2C}$ receptor antagonist, or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). The current invention also relates to combinations of a 5-$HT_{1A}$ receptor agonist, 5-$HT_{2A}$ receptor antagonist, 5-$HT_{2C}$ receptor antagonist, or combinations thereof (e.g., trazodone), and a norepinephrine-dopamine reuptake inhibitor (e.g. bupropion), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. The current invention also relates to combinations of a 5-$HT_{1A}$ receptor agonist, 5-$HT_{2A}$ receptor antagonist (e.g., trazodone, nefazodone, mirtazapine, flibanserin), a norepinephrine-dopamine reuptake inhibitor (e.g. bupropion), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. These combinations are particularly effective for each of these disorders as they allow the corrective effects of the individual agents to become manifest without being masked by the side effects of either drug, and in particular it allow rapid relief of symptoms because the effective dose can be given immediately due to the low expected side effects, instead of requiring weeks of up-titration to overcome side effects over time. Reduced toxicity is provided by a compound of the invention when administered in vivo, e.g., formulating bupropion, by itself a mild stimulant, with trazodone, by itself a moderate sedative, in the proprietary ratio of Lorexys, will neutralize the main side effects of each of the two drugs. This makes Lorexys®, a fixed combination of bupropion and trazodone, of special value for treating acute symptoms such as suicidality, disabling symptoms such as inability to work or otherwise function, especially for older patients who generally are more prone to side effects and for whom adverse effects cause more risk, and especially because such a combination can be prescribed by a health provider with less specialized expertise in pharmacologic treatment of neuro-psychiatric disorders.

The current invention also relates to combinations of a 5-$HT_{1A}$ receptor agonist and/or 5-$HT_{2A}$ receptor antagonist (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), and/or a 5-$HT_{2C}$ receptor antagonist, and/or a 5HT-2c receptor agonist, (e.g., lorcaserin, vabicaserin, PRX-00933, YM348, and metachlorophenylpiperazine, mCPP), a norepinephrine-dopamine reuptake inhibitor (e.g., bupropion), and/or other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. The current invention also relates to combinations of a 5-$HT_{1A}$ receptor agonist, 5-$HT_{2A}$ receptor antagonist (e.g., trazodone, nefazodone, mirtazapine, flibanserin), a norepinephrine-dopamine reuptake inhibitor (e.g. bupropion), and/or an oxytocin receptor (OXTR) agonist (e.g., carbetocin, oxytocin, Syntocinon®) to augment cognition, improve failing mental processes in cognitive disorders, and improve mood and the depressive symptoms that accompany mood disorders. These combinations are particularly effective for each of these disorders as they allow the corrective effects of the individual agents to become manifest without being masked by the side effects of either drug, and in particular it allow rapid relief of symptoms because the effective dose can be given immediately due to the low expected side effects, instead of requiring weeks of up-titration to overcome side effects over time. Reduced toxicity is provided by a compound of the invention when administered in vivo, e.g., formulating bupropion, by itself a mild stimulant, with trazodone, by itself a moderate sedative, in the proprietary ratio of Lorexys, will neutralize the main side effects of each of the two drugs. This makes Lorexys®, a fixed combination of bupropion and trazodone, of special value for treating acute symptoms such as suicidality, disabling symptoms such as inability to work or otherwise function, especially for older patients who generally are more prone to side effects and for whom adverse effects cause more risk, and especially because such a combination can be prescribed by a health provider with less specialized expertise in pharmacologic treatment of neuro-psychiatric disorders.

SUMMARY OF THE INVENTION

In one aspect, the invention provides compositions and methods of treating a subject suffering from or susceptible to a sexual disorder or symptom thereof (e.g., HSDD, FSAD, FOD, erectile disorder, male sexual performance anxiety, sexual interest-arousal disorder, female sexual dysfunction (FSD), male sexual dysfunction (MSD), and the like) comprising administering to a subject in need thereof a therapeutically effective amount of a composition delineated herein.

The current invention relates to combinations of a 5-$HT_{1A}$ receptor agonist, 5-$HT_{2A}$ receptor antagonist, 5-$HT_{2C}$ receptor antagonist, or combinations thereof (e.g., trazodone).

The current invention also relates to combinations of a 5-HT$_{1A}$ receptor agonist, 5-HT$_{2A}$ receptor antagonist, 5-HT$_{2C}$ receptor antagonist, or combinations thereof (e.g., trazodone), and a norepinephrine-dopamine reuptake inhibitor (e.g. bupropion), and/or an oxytocin receptor (OXTR) agonist (e.g., carbetocin, oxytocin, Syntocinon®).

The current invention relates to combinations of a 5-HT$_{1A}$ receptor agonist, 5-HT$_{2A}$ receptor antagonist, 5-HT$_{2C}$ receptor antagonist, or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). The current invention also relates to combinations of a 5-HT$_{1A}$ receptor agonist, 5-HT$_{2A}$ receptor antagonist, 5-HT$_{2C}$ receptor antagonist, or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), and a norepinephrine-dopamine reuptake inhibitor (e.g. bupropion), and/or an oxytocin receptor (OXTR) agonist (e.g., carbetocin, oxytocin, Syntocinon®).

The current invention relates to combinations of a 5-HT$_{1A}$ receptor agonist, 5-HT$_{2A}$ receptor antagonist, 5-HT$_{2C}$ receptor antagonist, or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). The current invention also relates to combinations of a 5-HT$_{1A}$ receptor agonist, 5-HT$_{2A}$ receptor antagonist, 5-HT$_{2C}$ receptor antagonist, or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), and/or a norepinephrine-dopamine reuptake inhibitor (e.g. bupropion), and/or an oxytocin receptor (OXTR) agonist (e.g., carbetocin, oxytocin, Syntocinon®), and/or other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba).

The current invention relates to combinations of a 5-HT$_{1A}$ receptor agonist, 5-HT$_{2A}$ receptor antagonist, 5-HT$_{2C}$ receptor antagonist, a 5-HT$_{2C}$ receptor agonist (e.g., lorcaserin, vabicaserin, PRX-00933, YM348, and metachlorophenylpiperazine, mCPP) or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). The current invention also relates to combinations of a 5-HT$_{1A}$ receptor agonist, 5-HT$_{2A}$ receptor antagonist, 5-HT$_{2C}$ receptor antagonist, a 5-HT$_{2C}$ receptor agonist (e.g., lorcaserin, vabicaserin, PRX-00933, YM348, and metachlorophenylpiperazine, mCPP), or combinations thereof (e.g., trazodone, nefazodone, mirtazapine, flibanserin ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), and/or a norepinephrine-dopamine reuptake inhibitor (e.g. bupropion), and/or other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and/or an oxytocin receptor (OXTR) agonist (e.g., carbetocin, oxytocin, Syntocinon®).

In one aspect, the invention provides a composition comprising a 5-HT$_{2A}$ antagonist, a norepinephrine-dopamine reuptake inhibitor, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone and bupropion. In another aspect the composition is that comprising trazodone in a dosage range of 1-450 mg and bupropion in a dosage range of 1-450 mg.

In one aspect, the invention provides a composition comprising a 5-HT$_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone, bupropion, and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and ginkgo biloba. In another aspect the composition is that comprising trazodone in a dosage range of 1-450 mg and bupropion in a dosage range of 1-450 mg.

In one aspect, the invention provides a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, and metachlorophenylpiperazine, mCPP) and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone, bupropion, and one or more 5-HT$_{2C}$ agonists selected from the group consisting of lorcaserin, vabicaserin, PRX-00933, YM348, and metachlorophenylpiperazine, and mCPP. In another aspect the composition is that comprising trazodone in a dosage range of 1-450 mg and bupropion in a dosage range of 1-450 mg.

In one aspect, the invention provides a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, and metachlorophenylpiperazine, mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; bupropion; one or more 5-HT$_{2C}$ agonists selected from the group consisting of lorcaserin, vabicaserin, PRX-00933, YM348, metachlorophenylpiperazine, and mCPP; and at least one of the group consisting of atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising trazodone in a dosage range of 1-450 mg and bupropion in a dosage range of 1-450 mg.

In one aspect, the invention provides a composition comprising a 5-HT$_{2A}$ antagonist, a norepinephrine-dopamine reuptake inhibitor, and an oxytocin receptor (OXTR) agonist, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone, bupropion, and oxytocin (e.g., Syntocinon®). In another aspect the composition is that comprising trazodone in a dosage range of 1-450 mg, bupropion in a dosage range of 1-450 mg, and oxytocin in a dosage range of 4-400 International Units.

In one aspect, the invention provides a composition comprising a 5-HT$_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and an oxytocin receptor (OXTR) agonist, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; bupropion; at least one of the group consisting of atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*; and oxytocin (e.g., Syntocinon®). In another aspect the composition is that comprising trazodone in a dosage range of 1-450 mg, bupropion in a dosage range of 1-450 mg, and oxytocin in a dosage range of 4-400 International Units.

In one aspect, the invention provides a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, and metachlorophenylpiperazine, mCPP), an oxytocin receptor (OXTR) agonist, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone, bupropion, oxytocin (e.g., Syntocinon®), and one or more 5-HT$_{2C}$ agonists selected from the group consisting of lorcaserin, vabicaserin, PRX-00933, YM348, metachlorophenylpiperazine, and mCPP. In another aspect the composition is that comprising trazodone in a dosage range of 1-450 mg, bupropion in a dosage range of 1-450 mg, and oxytocin in a dosage range of 4-400 International Units.

In one aspect, the invention provides a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, and metachlorophenylpiperazine, mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an oxytocin receptor (OXTR) agonist, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; bupropion; oxytocin (e.g., Syntocinon®); one or more 5-HT$_{2C}$ agonists selected from the group consisting of lorcaserin, vabicaserin, PRX-00933, YM348, metachlorophenylpiperazine, and mCPP; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising trazodone in a dosage range of 1-450 mg, bupropion in a dosage range of 1-450 mg, and oxytocin in a dosage range of 4-400 International Units.

In one aspect, the invention provides a composition comprising a 5-HT$_{2A}$ antagonist, an oxytocin receptor (OXTR) agonist, and a pharmaceutically acceptable carrier. In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone and oxytocin. In another aspect the composition is that comprising trazodone in a dosage range of 25-450 mg and oxytocin in a dosage range of 4-400 International Units.

In one aspect, the invention provides a composition comprising a 5-HT$_{2A}$ antagonist, an oxytocin receptor (OXTR) agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; oxytocin; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising trazodone in a dosage range of 25-450 mg and oxytocin in a dosage range of 4-400 International Units.

In one aspect, the invention provides a composition comprising a 5-HT$_{2A}$ antagonist, an oxytocin receptor (OXTR) agonist, a 5-HT$_{2C}$ agonist (e.g., lorcaserin, vabicaserin, PRX-00933, YM348, metachlorophenylpiperazine, and mCPP) and a pharmaceutically acceptable carrier. In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; oxytocin; and one or more 5-HT$_{2C}$ agonists selected from the group consisting of lorcaserin, vabicaserin, PRX-00933, YM348, metachlorophenylpiperazine, and mCPP. In another aspect the composition is that comprising trazodone in a dosage range of 25-450 mg and oxytocin in a dosage range of 4-400 International Units.

In one aspect, the invention provides a composition comprising a 5-HT$_{2A}$ antagonist, an oxytocin receptor (OXTR) agonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that wherein the 5-HT$_{2A}$ antagonist is also a 5-HT$_{1A}$ receptor agonist. In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone). In another aspect the composition is that comprising trazodone; oxytocin; one or more 5-HT$_{2C}$ agonists selected from the group consisting of lorcaserin, vabicaserin, PRX-00933, YM348, metachlorophenylpiperazine, and mCPP; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising trazodone in a dosage range of 25-450 mg and oxytocin in a dosage range of 4-400 International Units.

In one aspect, the invention provides a composition comprising a norepinephrine-dopamine reuptake inhibitor, an oxytocin receptor (OXTR) agonist, and a pharmaceutically acceptable carrier. In another aspect the composition is that comprising bupropion and oxytocin. In another aspect the composition is that comprising bupropion in a dosage range of 200-450 mg and oxytocin in a dosage range of 4-400 International Units. In another aspect the composition is that comprising bupropion in a dosage range of 25-450 mg and oxytocin in a dosage range of 4-400 International Units.

In one aspect, the invention provides a composition comprising a norepinephrine-dopamine reuptake inhibitor, an oxytocin receptor (OXTR) agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that comprising bupropion; oxytocin; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising bupropion in a dosage range of 200-450 mg and oxytocin in a dosage range of 4-400 International Units. In another aspect the composition is that comprising bupropion in a dosage range of 25-450 mg and oxytocin in a dosage range of 4-400 International Units.

In one aspect, the invention provides a composition comprising a norepinephrine-dopamine reuptake inhibitor, an oxytocin receptor (OXTR) agonist, a 5-HT$_{2C}$ agonist (e.g., lorcaserin, vabicaserin, PRX-00933, YM348, metachlorophenylpiperazine, and mCPP), and a pharmaceutically acceptable carrier. In another aspect the composition is that comprising bupropion; oxytocin; and one or more 5-HT$_{2C}$ agonists selected from the group consisting of lorcaserin, vabicaserin, PRX-00933, YM348, metachlorophenylpiperazine, and mCPP. In another aspect the composition is that comprising bupropion in a dosage range of 200-450 mg and oxytocin in a dosage range of 4-400 International Units. In another aspect the composition is that comprising bupropion in a dosage range of 25-450 mg and oxytocin in a dosage range of 4-400 International Units.

In one aspect, the invention provides a composition comprising a norepinephrine-dopamine reuptake inhibitor, an oxytocin receptor (OXTR) agonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that comprising bupropion; oxytocin; one or more 5-HT$_{2C}$ agonists selected from the group consisting of lorcaserin, vabicaserin, PRX-00933, YM348, metachlorophenylpiperazine, and mCPP; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising bupropion in a dosage range of 200-450 mg and oxytocin in a dosage range of 4-400 International Units. In another aspect the composition is that comprising bupropion in a dosage range of 25-450 mg and oxytocin in a dosage range of 4-400 International Units.

In one aspect, the invention provides a composition comprising an oxytocin receptor (OXTR) agonist and a pharmaceutically acceptable carrier. In another aspect the composition is that comprising oxytocin. In another aspect the composition is that comprising oxytocin in a dosage range of 4-400 International Units.

In one aspect, the invention provides a composition comprising an oxytocin receptor (OXTR) agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that comprising oxytocin and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and *ginkgo biloba*. In another aspect the composition is that comprising oxytocin in a dosage range of 4-400 International Units.

In one aspect, the invention provides a composition comprising an oxytocin receptor (OXTR) agonist, a 5-HT$_{2C}$ agonist (e.g., lorcaserin, vabicaserin, PRX-00933, YM348, metachlorophenylpiperazine, and mCPP), and a pharmaceutically acceptable carrier. In another aspect the composition is that comprising oxytocin and one or more 5-HT$_{2C}$ agonists selected from the group consisting of lorcaserin, vabicaserin, PRX-00933, YM348, metachlorophenylpiperazine, and mCPP. In another aspect the composition is that comprising oxytocin in a dosage range of 4-400 International Units.

In one aspect, the invention provides a composition comprising an oxytocin receptor (OXTR) agonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In another aspect the composition is that comprising oxytocin; one or more 5-$HT_{2C}$ agonists selected from the group consisting of lorcaserin, vabicaserin, PRX-00933, YM348, metachlorophenylpiperazine, and mCPP; and at least one of the group consisting of atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, and ginkgo biloba. In another aspect the composition is that comprising oxytocin in a dosage range of 4-400 International Units.

In one embodiment, the composition is that comprising bupropion, comprising bupropion in a dosage range of 200-450 mg; comprising bupropion in a dosage range of 225-300 mg; or comprising bupropion in a dosage range of 200-275 mg; comprising bupropion in a dosage range of 100-450 mg; comprising bupropion in a dosage range of 100-275 mg; comprising bupropion in a dosage range of 25-275 mg; comprising bupropion in a dosage range of XX-YY mg, wherein XX is an integer between 5 and 400 and YY is an integer between 50 and 450.

In one embodiment, the composition is that comprising trazodone, comprising trazodone in a dosage range of 25-450 mg; comprising trazodone in a dosage range of 75-150 mg; or comprising trazodone in a dosage range of 50-100 mg; comprising trazodone in a dosage range of XX-YY mg, wherein XX is an integer between 25 and 400 and YY is an integer between 50 and 450.

In one embodiment, the composition is that comprising oxytocin, comprising oxytocin in a dosage range of 4-400 International Units.

In one aspect, the invention provides a method of treating a subject suffering from or susceptible to a sexual disorder comprising administering to a subject in need thereof a therapeutically effective amount of a composition comprising a 5-$HT_{2A}$ antagonist, a norepinephrine-dopamine reuptake inhibitor, and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-$HT_{2A}$ antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-$HT_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-$HT_{2A}$ antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-$HT_{2A}$ antagonist, a norepinephrine-dopamine reuptake inhibitor, a 5-$HT_{2C}$ agonist (e.g., lorcaserin, vabicaserin, PRX-00933, YM348, metachlorophenylpiperazine, and mCPP), and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-$HT_{2A}$ antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-$HT_{2A}$ antagonist, a norepinephrine-dopamine reuptake inhibitor, a 5-$HT_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In another aspect the composition is that wherein the norepinephrine-dopamine reuptake inhibitor is also an alpha adrenergic blocker (e.g., bupropion). In another aspect the composition is that wherein the 5-$HT_{2A}$ antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin). In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist. (e.g., trazodone) In another aspect, the norepinephrine-dopamine reuptake inhibitor is also an alpha adrenergic blocker (e.g., bupropion). In another aspect, the alpha adrenergic blocker is also a 5-HT$_{2A}$ antagonist, a 5-HT$_{1A}$ receptor agonist, and/or 5-HT$_{2C}$ receptor antagonist (e.g., trazodone).

In one aspect, the invention provides a method of treating a subject suffering from or susceptible to a sexual disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist. (e.g., trazodone) In another aspect, the norepinephrine-dopamine reuptake inhibitor is also an alpha adrenergic blocker (e.g., bupropion). In another aspect, the alpha adrenergic blocker is also a 5-HT$_{2A}$ antagonist, a 5-HT$_{1A}$ receptor agonist, and/or 5-HT$_{2C}$ receptor antagonist (e.g., trazodone).

In one aspect, the invention provides a method of treating a subject suffering from or susceptible to a sexual disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ antagonist is also a 5-HT$_{2C}$ receptor antagonist.

In another aspect the composition is that wherein the 5-HT$_{2A}$ receptor antagonist is also a 5-HT$_{2C}$ receptor antagonist and a 5-HT$_{1A}$ receptor agonist. (e.g., trazodone) In another aspect, the norepinephrine-dopamine reuptake inhibitor is also an alpha adrenergic blocker (e.g., bupropion). In another aspect, the alpha adrenergic blocker is also a 5-HT$_{2A}$ antagonist, a 5-HT$_{1A}$ receptor agonist, and/or 5-HT$_{2C}$ receptor antagonist (e.g., trazodone).

In one aspect, the invention provides a method of treating a subject suffering from or susceptible to a sexual disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist. (e.g., trazodone) In another aspect, the norepinephrine-dopamine reuptake inhibitor is also an alpha adrenergic blocker (e.g., bupropion). In another aspect, the alpha adrenergic blocker is also a 5-HT$_{2A}$ antagonist, a 5-HT$_{1A}$ receptor agonist, and/or 5-HT$_{2C}$ receptor antagonist (e.g., trazodone).

In one aspect, the invention provides a method of treating a subject suffering from or susceptible to a sexual disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist. (e.g., trazodone) In another aspect, the norepinephrine-dopamine reuptake inhibitor is also an alpha adrenergic blocker (e.g., bupropion). In another aspect, the alpha adrenergic blocker is also a 5-HT$_{2A}$ antagonist, a 5-HT$_{1A}$ receptor agonist, and/or 5-HT$_{2C}$ receptor antagonist (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100, 907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), and a pharmaceutically acceptable carrier. In another aspect, the composition also includes an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect, the composition also includes an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), a $5\text{-HT}_{2C}$ agonist (e.g., lorcaserin, vabicaserin, PRX-00933, YM348, metachlorophenylpiperazine, and mCPP), and a pharmaceutically acceptable carrier. In another aspect, the composition also includes an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), a $5\text{-HT}_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect, the composition also includes an alpha adrenergic blocker (e.g., trazodone).

In one aspect, the invention provides a method of treating a subject suffering from or susceptible to a sexual disorder comprising administering to a subject in need thereof a therapeutically effective amount of a composition comprising an oxytocin receptor (OXTR) agonist (e.g., carbetocin, oxytocin, Syntocinon®) and a pharmaceutically acceptable carrier.

In one aspect, the invention provides a method of treating a subject suffering from or susceptible to a sexual disorder comprising administering to a subject in need thereof a therapeutically effective amount of a composition comprising an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In aspects, the method is that wherein the sexual disorder is female sexual disorder (FSD). In aspects, the method is that wherein the sexual disorder is female orgasmic disorder (FOD); wherein the sexual disorder is female sexual arousal disorder (FSAD); or wherein the sexual disorder is sexual pain disorder or dysfunction. In aspects, the method is that wherein the FSD includes one or more simultaneous dysfunctions of sexual desire, arousal, orgasm, and/or pain. In aspects, the method is that wherein the sexual disorder is male sexual disorder (MSD). In aspects, the method is that wherein the sexual disorder is male Hypoactive Sexual Desire Disorder (HSDD); wherein the sexual disorder is male sexual arousal disorder (FSAD); wherein the sexual disorder is male orgasmic disorder (MOD; delayed ejaculation); wherein the sexual disorder is premature ejaculation (PE); wherein the sexual dysfunction is sexual performance anxiety; or wherein the sexual disorder is sexual pain disorder or dysfunction. In aspects, the method is that wherein the MSD includes one or more simultaneous dysfunctions of sexual desire, arousal, orgasm, and/or pain.

In one aspect, the invention provides a method of treating a subject suffering from or susceptible to a cognitive disorder comprising administering to a subject in need thereof a therapeutically effective amount of a composition comprising a $5\text{-HT}_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a $5\text{-HT}_{2A}$ antagonist and a $5\text{-HT}_{1A}$ receptor agonist (e.g., trazodone, nefazodone, mirtazapine, flibanserin). In another aspect the composition is that wherein the norepinephrine-dopamine reuptake inhibitor is also an alpha adrenergic blocker (e.g., bupropion). In another aspect the composition is that wherein the $5\text{-HT}_{2A}$ receptor antagonist is also a $5\text{-HT}_{1A}$ receptor agonist. In another aspect the composition is that wherein the $5\text{-HT}_{2A}$ receptor antagonist is also a $5\text{-HT}_{2C}$ receptor antagonist. In another aspect the composition is that wherein the $5\text{-HT}_{2A}$ receptor antagonist is also a $5\text{-HT}_{2C}$ receptor antagonist and a $5\text{-HT}_{1A}$ receptor agonist (e.g., trazodone). In another aspect the composition is that wherein the $5\text{-HT}_{2A}$ receptor antagonist, $5\text{-HT}_{1A}$ receptor agonist, and/or $5\text{-HT}_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a $5\text{-HT}_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a $5\text{-HT}_{2A}$ antagonist and a $5\text{-HT}_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines). In another aspect the composition is that wherein the norepinephrine-dopamine reuptake inhibitor is also an alpha adrenergic blocker (e.g., bupropion). In another aspect the composition is that wherein the $5\text{-HT}_{2A}$ receptor antagonist is also a $5\text{-HT}_{1A}$ receptor agonist. In another aspect the composition is that wherein the $5\text{-HT}_{2A}$ receptor antagonist is also a $5\text{-HT}_{2C}$ receptor antagonist. In another aspect the composition is that wherein the $5\text{-HT}_{2A}$ receptor antagonist is also a $5\text{-HT}_{2C}$ receptor antagonist and a $5\text{-HT}_{1A}$ receptor agonist (e.g., trazodone). In another aspect the composition is that wherein the $5\text{-HT}_{2A}$ receptor antagonist, $5\text{-HT}_{1A}$ receptor agonist, and/or $5\text{-HT}_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a $5\text{-HT}_{2A}$ antagonist, a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100, 907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of treating a subject suffering from or susceptible to a cognitive disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), and a pharmaceutically acceptable carrier. In another aspect the composition is that wherein the norepinephrine-dopamine reuptake inhibitor is also an alpha adrenergic blocker (e.g., bupropion).

In one aspect, the invention provides a method of treating a subject suffering from or susceptible to a cognitive disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that wherein the norepinephrine-dopamine reuptake inhibitor is also an alpha adrenergic blocker (e.g., bupropion).

In one aspect, the invention provides a method of treating a subject suffering from or susceptible to a cognitive disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier. In another aspect the composition is that wherein the norepinephrine-dopamine reuptake inhibitor is also an alpha adrenergic blocker (e.g., bupropion).

In one aspect, the invention provides a method of treating a subject suffering from or susceptible to a cognitive disorder comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In another aspect the composition is that wherein the norepinephrine-dopamine reuptake inhibitor is also an alpha adrenergic blocker (e.g., bupropion).

In one aspect, the invention provides a method of treating a subject suffering from or susceptible to a cognitive disorder comprising administering to a subject in need thereof a therapeutically effective amount of a composition comprising an oxytocin receptor (OXTR) agonist (e.g., carbetocin, oxytocin, Syntocinon®) and a pharmaceutically acceptable carrier.

In one aspect, the invention provides a method of treating a subject suffering from or susceptible to a cognitive disorder comprising administering to a subject in need thereof a therapeutically effective amount of a composition comprising an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a method of treating a subject suffering from or susceptible to a cognitive disorder comprising administering to a subject in need thereof a therapeutically effective amount of a composition comprising an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a method of treating a subject suffering from or susceptible to a cognitive disorder comprising administering to a subject in need thereof a therapeutically effective amount of a composition comprising an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In aspects, the method is that wherein the cognitive disorder is dementia, where dementia can refer to Alzheimer's disease, frontotemporal lobar degeneration, dementia with Lewy bodies, Parkinson's disease, Huntington's disease, multi-infarct dementia, dementia resulting from infections affecting the central nervous system, dementia resulting from chronic drug use, dementia resulting from hydrocephalus, dementia resulting from brain injury, or dementia resulting from a brain tumor.

In aspects, the method is that wherein the cognitive disorder is cognitive disability, where cognitive disability can refer to schizophrenia, schizoaffective disorder, bipolar disorder, or major depression.

In aspects, the method is that wherein the cognitive disorder is cognitive disability, where cognitive disability can refer to schizophrenia, schizoaffective disorder, bipolar disorder, social anxiety disorder, or major depression.

In aspects, the method is that wherein the cognitive disorder is developmental cognitive impairment, where cognitive impairment can refer to Autism, Asperger's syndrome, or pervasive developmental disorder.

In aspects, the method is that wherein the cognitive disorder is mild cognitive decline.

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{2A}$ antagonist, a norepinephrine-dopamine reuptake inhibitor, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is both a 5-HT$_{2A}$ antagonist and a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the norepinephrine-dopamine reuptake inhibitor is also an alpha adrenergic blocker (e.g., bupropion). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin). In another aspect the composition is that wherein the 5-HT$_{2A}$ receptor antagonist is also a 5-HT$_{1A}$ receptor agonist. In another aspect the composition is that wherein the 5-HT$_{2A}$ receptor antagonist is also a 5-HT$_{2C}$ receptor antagonist. In another aspect the composition is that wherein the 5-HT$_{2A}$ receptor antagonist is also a 5-HT$_{2C}$ receptor antagonist and a 5-HT$_{1A}$ receptor agonist (e.g., trazodone). In another aspect the composition is that wherein the 5-HT$_{2A}$ receptor antagonist, 5-HT$_{1A}$ receptor agonist, and/or 5-HT$_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-HT$_{1A}$ receptor agonist, a 5-HT$_{2A}$ antagonist, an oxytocin receptor (OXTR) agonist (e.g., carbetocin, oxytocin, Syntocinon®), and a pharmaceutically acceptable carrier. In one aspect, one compound is the 5-HT$_{1A}$ receptor agonist and the 5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-$HT_{2A}$ receptor antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-$HT_{1A}$ receptor agonist, a 5-$HT_{2A}$ antagonist, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In one aspect, one compound is the 5-$HT_{1A}$ receptor agonist and the 5-$HT_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-$HT_{2A}$ receptor antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-$HT_{1A}$ receptor agonist, a 5-$HT_{2A}$ antagonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine, and mCPP), and a pharmaceutically acceptable carrier. In one aspect, one compound is the 5-$HT_{1A}$ receptor agonist and the 5-$HT_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-$HT_{2A}$ receptor antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a 5-$HT_{1A}$ receptor agonist, a 5-$HT_{2A}$ antagonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In one aspect, one compound is the 5-$HT_{1A}$ receptor agonist and the 5-$HT_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines). In another aspect the composition is that wherein the 5-$HT_{2A}$ receptor antagonist is also a 5-$HT_{1A}$ receptor agonist. In another aspect the composition is that wherein the 5-$HT_{2A}$ receptor antagonist is also a 5-$HT_{2C}$ receptor antagonist. In another aspect the composition is that wherein the 5-$HT_{2A}$ receptor antagonist is also a 5-$HT_{2C}$ receptor antagonist and a 5-$HT_{1A}$ receptor agonist (e.g., trazodone). In another aspect the composition is that wherein the 5-$HT_{2A}$ receptor antagonist, 5-$HT_{1A}$ receptor agonist, and/or 5-$HT_{2C}$ receptor antagonist is also an alpha adrenergic blocker (e.g., trazodone).

In one aspect, the invention provides a method of enhancing cognition comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), and a pharmaceutically acceptable carrier. In another aspect, the norepinephrine-dopamine reuptake inhibitor is also a alpha adrenergic blocker (e.g., bupropion).

In one aspect, the invention provides a method of enhancing cognition comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and a pharmaceutically acceptable carrier. In another aspect, the norepinephrine-dopamine reuptake inhibitor is also a alpha adrenergic blocker (e.g., bupropion).

In one aspect, the invention provides a method of enhancing cognition comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine, and mCPP), and a pharmaceutically acceptable carrier. In another aspect, the norepinephrine-dopamine reuptake inhibitor is also a alpha adrenergic blocker (e.g., bupropion).

In one aspect, the invention provides a method of enhancing cognition comprising administering to a subject in need thereof a therapeutically effective amount of a composition comprising a norepinephrine-dopamine reuptake inhibitor, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), a 5-$HT_{2C}$ agonist (e.g., lorcaserin, vabicaserin, PRX-00933, YM348, metachlorophenylpiperazine, and mCPP), and a pharmaceutically acceptable carrier. In another aspect, the norepinephrine-dopamine reuptake inhibitor is also a alpha adrenergic blocker (e.g., bupropion).

In one aspect, the invention provides a method of enhancing cognition comprising administering to a subject in need thereof a therapeutically effective amount of a composition comprising an oxytocin receptor (OXTR) agonist (e.g., carbetocin, oxytocin, Syntocinon®) and a pharmaceutically acceptable carrier.

In one aspect, the invention provides a method of enhancing cognition comprising administering to a subject in need thereof a therapeutically effective amount of a composition comprising an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a method of enhancing cognition comprising administering to a subject in need thereof a therapeutically effective amount of a composition comprising an oxytocin receptor (OXTR) agonist (e.g., carbetocin, oxytocin, Syntocinon®, a 5-$HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a method of enhancing cognition comprising administering to a subject in need thereof a therapeutically effective amount of a composition comprising an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), a 5-$HT_{2C}$ agonist (e.g., lorcaserin, vabicaserin, PRX-00933, YM348, metachlorophenylpiperazine, and mCPP), and a pharmaceutically acceptable carrier.

In aspects, the method is that wherein the cognition enhancement is improving mental activities such as attention, perception, learning, memory, language, planning, decision-making, organization, conceptualization, reorganization, synthesis of facts, synthesis of data, recall, calculation, spatiotemporal visualization, mental flexibility, creativity, or the ability to accept challenging intellectual or cultural pursuits.

Another aspect is a method of treating a disease, disorder or symptom thereof described in the Diagnostic and Statistical Manual of Mental Disorders (DSM-IV-TR) in a subject comprising administering to the subject a compound or composition herein.

Another aspect is a method of treating erectile dysfunction (ED) in a subject comprising administering to the subject a compound or composition herein.

Another aspect is a method of treating male HSDD in a subject comprising administering to the subject a compound or composition herein.

Another aspect is a method of treating male sexual disorders in a subject comprising administering to the subject a compound or composition herein.

Another aspect is a method of treating depressive disorders in a subject comprising administering to the subject a compound or composition herein. Depressive disorders and "depression" as used in this document includes each of the depressive disorder recognized and defined by the DSM-IV-TR: Major Depressive Disorder and Major Depressive Episode (MDD/MDE: at least five major symptoms such as impairment of ability to work and suicidality nearly every day for at least two weeks), Mood Disorder due to a General Medical Condition, Substance-Induced Mood Disorder, and Depressive Disorder Not Otherwise Specified. Each of these disorders includes specifiers of With or Without Psychotic Features, With Catatonic Features (or without), With Melancholic Features (or without), With Atypical Features (or without), and With Postpartum Onset. Lesser depressive disorders, but still associated with significant disability, include Dysthymic Disorder (lesser symptoms such as low energy but not loss of pleasure in all activities; feelings of hopeless but not suicidality, on a majority of days for at least two years) and Depressive Disorder Not Otherwise Specified (too few symptoms or too little constancy to meet criteria for MDD/MDE but still causing disability, including premenstrual dysphoric disorder, minor depressive disorder (less than 5 depressive symptoms), recurrent brief depressive disorder (episodes lasting less than 2 weeks), post-psychotic depressive disorder of Schizophrenia.

Another aspect is an extended release composition comprising a 5-$HT_{2A}$ antagonist, a norepinephrine-dopamine reuptake inhibitor (e.g., bupropion), and a pharmaceutically acceptable carrier.

Another aspect is an extended release composition comprising a 5-$HT_{2A}$ antagonist, a norepinephrine-dopamine reuptake inhibitor (e.g., bupropion), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a 5-$HT_{2A}$ antagonist, a norepinephrine-dopamine reuptake inhibitor (e.g., bupropion), a 5-$HT_{2C}$ agonist (e.g., lorcaserin, vabicaserin, PRX-00933, YM348, metachlorophenylpiperazine, and mCPP), and a pharmaceutically acceptable carrier.

Another aspect is an extended release composition comprising a 5-$HT_{2A}$ antagonist, a norepinephrine-dopamine reuptake inhibitor (e.g., bupropion), a 5-$HT_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a 5-HT$_{2A}$ antagonist, a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier.

Another aspect is an extended release composition comprising a 5-HT$_{2A}$ antagonist, a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a 5-HT$_{2A}$ antagonist, a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier.

Another aspect is an extended release composition comprising a 5-HT$_{2A}$ antagonist, a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a 5-HT$_{2A}$ antagonist, an oxytocin receptor (OXTR) agonist (e.g., carbetocin, oxytocin, Syntocinon®), and a pharmaceutically acceptable carrier.

Another aspect is an extended release composition comprising a 5-HT$_{2A}$ antagonist, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier.

Another aspect is an extended release composition comprising a 5-HT$_{2A}$ antagonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier.

Another aspect is an extended release composition comprising a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier.

Another aspect is an extended release composition comprising a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising an oxytocin receptor (OXTR) agonist (e.g., carbetocin, oxytocin, Syntocinon®) and a pharmaceutically acceptable carrier.

Another aspect is an extended release composition comprising an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Another aspect is an extended release composition comprising an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), and a pharmaceutically acceptable carrier.

Another aspect is an extended release composition comprising an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist nefazodone and a pharmaceutically acceptable carrier.

In one aspect, the invention provides a composition comprising the 5-HT$_{1A}$ receptor agonist, and 5-HT$_{2A}$ antagonist nefazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist nefazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist nefazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist mirtazapine and a pharmaceutically acceptable carrier.

In one aspect, the invention provides a composition comprising the 5-HT$_{1A}$ receptor agonist, and 5-HT$_{2A}$ antagonist mirtazapine, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist mirtazapine, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist mirtazapine, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin and a pharmaceutically acceptable carrier.

In one aspect, the invention provides a composition comprising the 5-HT$_{1A}$ receptor agonist, and 5-HT$_{2A}$ antagonist flibanserin, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist, 5-HT$_{2A}$ receptor antagonist, and/or 5-HT$_{2C}$ receptor antagonist trazodone and a pharmaceutically acceptable carrier.

In one aspect, the invention provides a composition comprising the 5-HT$_{1A}$ receptor agonist, and 5-HT$_{2A}$ antagonist trazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

Other aspects include those, wherein the composition is administered orally; wherein the composition is administered topically; wherein the subject is diagnosed and being treated for depression; wherein the subject is not undergoing treatment for depression; wherein the subject is concurrently prescribed an additional therapeutic agent; or wherein the subject is concurrently not prescribed an additional therapeutic agent; wherein the subject is concurrently administered an additional therapeutic agent; or wherein the subject is concurrently not administered an additional therapeutic agent.

In one aspect, the invention provides a composition comprising a $5\text{-}HT_{1A}$ receptor agonist, a $5\text{-}HT_{2A}$ antagonist, and a pharmaceutically acceptable carrier.

In one aspect, the invention provides a composition comprising the $5\text{-}HT_{1A}$ receptor agonist, and $5\text{-}HT_{2A}$ antagonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist, a $5\text{-}HT_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In another aspect of the invention, a formulation of bupropion and trazodone to treat sexual disorders meets the specific concerns of men including onset of action within an hour and continuation of efficacy overnight after a dose.

In another aspect of the invention, a formulation of bupropion and trazodone to treat sexual disorders has a dose up to 50% larger of the two components compared to a formulation for women.

In another aspect of the invention, a formulation of bupropion and trazodone to treat sexual disorders has an outer layer with rapid release of an effective but well tolerated amount of trazodone and bupropion, and an inner core with a sustained release of an effective and well tolerated amount of trazodone and bupropion.

In another aspect of the invention, a formulation of bupropion and trazodone to treat sexual disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and trazodone to treat sexual disorders has an outer layer that releases a nontoxic dye in water or water-alcohol solutions (alcoholic drinks) sufficient in color to show that the drink has been tampered with.

In another aspect of the invention, a formulation of bupropion and trazodone to treat sexual disorders has an outer layer that releases a nontoxic gelling agent in water or water-alcohol solutions sufficient to thicken or solidify the drink to show it has been tampered with.

In one aspect, the invention provides a composition comprising the $5\text{-}HT_{1A}$ receptor agonist and $5\text{-}HT_{2A}$ antagonist nefazodone and a pharmaceutically acceptable carrier.

In one aspect, the invention provides a composition comprising the $5\text{-}HT_{1A}$ receptor agonist, and $5\text{-}HT_{2A}$ antagonist nefazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist nefazodone, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist nefazodone, a $5\text{-}HT_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist mirtazapine and a pharmaceutically acceptable carrier.

In one aspect, the invention provides a composition comprising the $5\text{-}HT_{1A}$ receptor agonist, and $5\text{-}HT_{2A}$ antagonist mirtazapine, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist mirtazapine, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist mirtazapine, a $5\text{-}HT_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin and a pharmaceutically acceptable carrier.

In one aspect, the invention provides a composition comprising the 5-HT$_{1A}$ receptor agonist, and 5-HT$_{2A}$ antagonist flibanserin, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist, 5-HT$_{2A}$ receptor antagonist, and/or 5-HT$_{2C}$ receptor antagonist trazodone and a pharmaceutically acceptable carrier.

In one aspect, the invention provides a composition comprising the 5-HT$_{1A}$ receptor agonist, and 5-HT$_{2A}$ antagonist trazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In another aspect of the invention, a formulation of bupropion, trazodone, and oxytocin to treat sexual disorders has an outer layer with rapid release of an effective but well tolerated amount of bupropion, trazodone, and oxytocin, and an inner core with a sustained release of an effective and well tolerated amount of bupropion, trazodone, and oxytocin.

In another aspect of the invention, a formulation of bupropion, trazodone, and oxytocin to treat sexual disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion, trazodone, and oxytocin to treat sexual disorders has an outer layer that releases a nontoxic dye in water or water-alcohol solutions (alcoholic drinks) sufficient in color to show that the drink has been tampered with.

In another aspect of the invention, a formulation of bupropion, trazodone, and oxytocin to treat sexual disorders has an outer layer that releases a nontoxic gelling agent in water or water-alcohol solutions sufficient to thicken or solidify the drink to show it has been tampered with.

In another aspect of the invention, a formulation of bupropion and oxytocin to treat sexual disorders has an outer layer with rapid release of an effective but well tolerated amount of bupropion and oxytocin, and an inner core with a sustained release of an effective and well tolerated amount of bupropion and oxytocin.

In another aspect of the invention, a formulation of bupropion and oxytocin to treat sexual disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and oxytocin to treat sexual disorders has an outer layer that releases a nontoxic dye in water or water-alcohol solutions (alcoholic drinks) sufficient in color to show that the drink has been tampered with.

In another aspect of the invention, a formulation of bupropion and oxytocin to treat sexual disorders has an outer layer that releases a nontoxic gelling agent in water or water-alcohol solutions sufficient to thicken or solidify the drink to show it has been tampered with.

In another aspect of the invention, a formulation of trazodone and oxytocin to treat sexual disorders has an outer layer with rapid release of an effective but well tolerated amount of trazodone and oxytocin, and an inner core with a sustained release of an effective and well tolerated amount of trazodone and oxytocin.

In another aspect of the invention, a formulation of trazodone and oxytocin to treat sexual disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of trazodone and oxytocin to treat sexual disorders has an outer layer that releases a nontoxic dye in water or water-alcohol solutions (alcoholic drinks) sufficient in color to show that the drink has been tampered with.

In another aspect of the invention, a formulation of trazodone and oxytocin to treat sexual disorders has an outer layer that releases a nontoxic gelling agent in water or water-alcohol solutions sufficient to thicken or solidify the drink to show it has been tampered with.

In another aspect of the invention, a formulation of oxytocin to treat sexual disorders has an outer layer with rapid release of an effective but well tolerated amount of oxytocin, and an inner core with a sustained release of an effective and well tolerated amount of oxytocin.

In another aspect of the invention, a formulation of oxytocin to treat sexual disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of oxytocin to treat sexual disorders has an outer layer that releases a nontoxic dye in water or water-alcohol solutions (alcoholic drinks) sufficient in color to show that the drink has been tampered with.

In another aspect of the invention, a formulation of oxytocin to treat sexual disorders has an outer layer that releases a nontoxic gelling agent in water or water-alcohol solutions sufficient to thicken or solidify the drink to show it has been tampered with.

In another aspect of the invention, a formulation of bupropion and trazodone to treat cognitive disorders has an outer layer with rapid release of an effective but well tolerated amount of trazodone and bupropion, and an inner core with a sustained release of an effective and well tolerated amount of trazodone and bupropion.

In another aspect of the invention, a formulation of bupropion and trazodone to treat cognitive disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and trazodone to treat cognitive disorders has an outer layer that releases a nontoxic dye in water or water-alcohol solutions (alcoholic drinks) sufficient in color to show that the drink has been tampered with.

In another aspect of the invention, a formulation of bupropion and trazodone to treat cognitive disorders has an outer layer that releases a nontoxic gelling agent in water or water-alcohol solutions sufficient to thicken or solidify the drink to show it has been tampered with.

In one aspect, the invention provides a composition comprising the $5\text{-}HT_{1A}$ receptor agonist and $5\text{-}HT_{2A}$ antagonist nefazodone and a pharmaceutically acceptable carrier.

In one aspect, the invention provides a composition comprising the $5\text{-}HT_{1A}$ receptor agonist, and $5\text{-}HT_{2A}$ antagonist nefazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist nefazodone, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist nefazodone, a $5\text{-}HT_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist mirtazapine and a pharmaceutically acceptable carrier.

In one aspect, the invention provides a composition comprising the $5\text{-}HT_{1A}$ receptor agonist, and $5\text{-}HT_{2A}$ antagonist mirtazapine, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist mirtazapine, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist mirtazapine, a $5\text{-}HT_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist flibanserin and a pharmaceutically acceptable carrier.

In one aspect, the invention provides a composition comprising the $5\text{-}HT_{1A}$ receptor agonist, and $5\text{-}HT_{2A}$ antagonist flibanserin, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the $5\text{-}HT_{1A}$ receptor agonist and $5\text{-}HT_{2A}$ antagonist flibanserin, a $5\text{-}HT_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the $5\text{-}HT_{1A}$ receptor agonist and $5\text{-}HT_{2A}$ antagonist flibanserin, a $5\text{-}HT_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising a $5\text{-}HT_{1A}$ receptor agonist, $5\text{-}HT_{2A}$ receptor antagonist, and/or $5\text{-}HT_{2C}$ receptor antagonist trazodone and a pharmaceutically acceptable carrier.

In one aspect, the invention provides a composition comprising the 5-HT$_{1A}$ receptor agonist, and 5-HT$_{2A}$ antagonist trazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In another aspect of the invention, a formulation of bupropion, trazodone, and oxytocin to treat cognitive disorders has an outer layer with rapid release of an effective but well tolerated amount of bupropion, trazodone, and oxytocin, and an inner core with a sustained release of an effective and well tolerated amount of bupropion, trazodone, and oxytocin.

In another aspect of the invention, a formulation of bupropion, trazodone, and oxytocin to treat cognitive disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion, trazodone, and oxytocin to treat cognitive disorders has an outer layer that releases a nontoxic dye in water or water-alcohol solutions (alcoholic drinks) sufficient in color to show that the drink has been tampered with.

In another aspect of the invention, a formulation of bupropion, trazodone, and oxytocin to treat cognitive disorders has an outer layer that releases a nontoxic gelling agent in water or water-alcohol solutions sufficient to thicken or solidify the drink to show it has been tampered with.

In another aspect of the invention, a formulation of bupropion and oxytocin to treat cognitive disorders has an outer layer with rapid release of an effective but well tolerated amount of bupropion and oxytocin, and an inner core with a sustained release of an effective and well tolerated amount of bupropion and oxytocin.

In another aspect of the invention, a formulation of bupropion and oxytocin to treat cognitive disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and oxytocin to treat cognitive disorders has an outer layer that releases a nontoxic dye in water or water-alcohol solutions (alcoholic drinks) sufficient in color to show that the drink has been tampered with.

In another aspect of the invention, a formulation of bupropion and oxytocin to treat cognitive disorders has an outer layer that releases a nontoxic gelling agent in water or water-alcohol solutions sufficient to thicken or solidify the drink to show it has been tampered with.

In another aspect of the invention, a formulation of trazodone and oxytocin to treat cognitive disorders has an outer layer with rapid release of an effective but well tolerated amount of trazodone and oxytocin, and an inner core with a sustained release of an effective and well tolerated amount of trazodone and oxytocin.

In another aspect of the invention, a formulation of trazodone and oxytocin to treat cognitive disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of trazodone and oxytocin to treat cognitive disorders has an outer layer that releases a nontoxic dye in water or water-alcohol solutions (alcoholic drinks) sufficient in color to show that the drink has been tampered with.

In another aspect of the invention, a formulation of trazodone and oxytocin to treat cognitive disorders has an outer layer that releases a nontoxic gelling agent in water or water-alcohol solutions sufficient to thicken or solidify the drink to show it has been tampered with.

In another aspect of the invention, a formulation of oxytocin to treat cognitive disorders has an outer layer with rapid release of an effective but well tolerated amount of oxytocin, and an inner core with a sustained release of an effective and well tolerated amount of oxytocin.

In another aspect of the invention, a formulation of oxytocin to treat cognitive disorders has a highly soluble outer layer and a matrix inner layer that remains insoluble in water or water-alcohol solutions (alcoholic drinks) and is large enough to be easily visible and show that the drink has been tampered with.

In another aspect of the invention, a formulation of oxytocin to treat cognitive disorders has an outer layer that releases a nontoxic dye in water or water-alcohol solutions (alcoholic drinks) sufficient in color to show that the drink has been tampered with.

In another aspect of the invention, a formulation of oxytocin to treat cognitive disorders has an outer layer that releases a nontoxic gelling agent in water or water-alcohol solutions sufficient to thicken or solidify the drink to show it has been tampered with.

In another aspect of the invention, a formulation of bupropion and trazodone to enhance cognition has an outer layer with rapid release of an effective but well tolerated amount of trazodone and bupropion, and an inner core with a sustained release of an effective and well tolerated amount of trazodone and bupropion.

In another aspect of the invention, a formulation of bupropion and trazodone to enhance cognition has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and trazodone to enhance cognition has an outer layer that releases a nontoxic dye in water or water-alcohol solutions (alcoholic drinks) sufficient in color to show that the drink has been tampered with.

In another aspect of the invention, a formulation of bupropion and trazodone to enhance cognition has an outer layer that releases a nontoxic gelling agent in water or water-alcohol solutions sufficient to thicken or solidify the drink to show it has been tampered with.

In one aspect, the invention provides a composition comprising the 5-HT$_{1A}$ receptor agonist and 5-HT$_{2A}$ antagonist nefazodone and a pharmaceutically acceptable carrier.

In one aspect, the invention provides a composition comprising the 5-HT$_{1A}$ receptor agonist, and 5-HT$_{2A}$ antagonist nefazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist nefazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist nefazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist mirtazapine and a pharmaceutically acceptable carrier.

In one aspect, the invention provides a composition comprising the 5-HT$_{1A}$ receptor agonist, and 5-HT$_{2A}$ antagonist mirtazapine, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist mirtazapine, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist mirtazapine, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin and a pharmaceutically acceptable carrier.

In one aspect, the invention provides a composition comprising the 5-HT$_{1A}$ receptor agonist, and 5-HT$_{2A}$ antagonist flibanserin, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist flibanserin, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising a 5-HT$_{1A}$ receptor agonist, 5-HT$_{2A}$ receptor antagonist, and/or 5-HT$_{2C}$ receptor antagonist trazodone and a pharmaceutically acceptable carrier.

In one aspect, the invention provides a composition comprising the 5-HT$_{1A}$ receptor agonist, and 5-HT$_{2A}$ antagonist trazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one aspect, the invention provides a composition comprising the 5-HT$_{1A}$ receptor agonist and 5-HT$_{2A}$ antagonist trazodone, a 5-HT$_{2C}$ agonist (e.g., lorcaserin, vabicaserin, PRX-00933, YM348, metachlorophenylpiperazine, and mCPP), ther non-abusable agents (agents not scheduled by the DEA) that augment dopamine and/or norepinephrine in the brain, e.g., atomoxetine, reboxetine, amedalin, CP-39, 332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In another aspect of the invention, a formulation of bupropion, trazodone, and oxytocin to enhance cognition has an outer layer with rapid release of an effective but well tolerated amount of bupropion, trazodone, and oxytocin, and an inner core with a sustained release of an effective and well tolerated amount of bupropion, trazodone, and oxytocin.

In another aspect of the invention, a formulation of bupropion, trazodone, and oxytocin to enhance cognition has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion, trazodone, and oxytocin to enhance cognition has an outer layer that releases a nontoxic dye in water or water-alcohol solutions (alcoholic drinks) sufficient in color to show that the drink has been tampered with.

In another aspect of the invention, a formulation of bupropion, trazodone, and oxytocin to enhance cognition has an outer layer that releases a nontoxic gelling agent in water or water-alcohol solutions sufficient to thicken or solidify the drink to show it has been tampered with.

In another aspect of the invention, a formulation of bupropion and oxytocin to enhance cognition has an outer layer with rapid release of an effective but well tolerated amount of bupropion and oxytocin, and an inner core with a sustained release of an effective and well tolerated amount of bupropion and oxytocin.

In another aspect of the invention, a formulation of bupropion and oxytocin to enhance cognition has a highly soluble outer layer and a matrix inner layer that remains insoluble in water or water-alcohol solutions (alcoholic drinks) and is large enough to be easily visible and show that the drink has been tampered with.

In another aspect of the invention, a formulation of bupropion and oxytocin to enhance cognition has an outer layer that releases a nontoxic dye in water or water-alcohol solutions (alcoholic drinks) sufficient in color to show that the drink has been tampered with.

In another aspect of the invention, a formulation of bupropion and oxytocin to enhance cognition has an outer layer that releases a nontoxic gelling agent in water or water-alcohol solutions sufficient to thicken or solidify the drink to show it has been tampered with.

In another aspect of the invention, a formulation of trazodone and oxytocin to enhance cognition has an outer layer with rapid release of an effective but well tolerated amount of trazodone and oxytocin, and an inner core with a sustained release of an effective and well tolerated amount of trazodone and oxytocin.

In another aspect of the invention, a formulation of trazodone and oxytocin to enhance cognition has a highly soluble outer layer and a matrix inner layer that remains insoluble in water or water-alcohol solutions (alcoholic drinks) and is large enough to be easily visible and show that the drink has been tampered with.

In another aspect of the invention, a formulation of trazodone and oxytocin to enhance cognition has an outer layer that releases a nontoxic dye in water or water-alcohol solutions (alcoholic drinks) sufficient in color to show that the drink has been tampered with.

In another aspect of the invention, a formulation of trazodone and oxytocin to enhance cognition has an outer layer that releases a nontoxic gelling agent in water or water-alcohol solutions sufficient to thicken or solidify the drink to show it has been tampered with.

In another aspect of the invention, a formulation of oxytocin to enhance cognition has an outer layer with rapid release of an effective but well tolerated amount of oxytocin, and an inner core with a sustained release of an effective and well tolerated amount of oxytocin.

In another aspect of the invention, a formulation of oxytocin to enhance cognition has a highly soluble outer layer and a matrix inner layer that remains insoluble in water or water-alcohol solutions (alcoholic drinks) and is large enough to be easily visible and show that the drink has been tampered with.

In another aspect of the invention, a formulation of oxytocin to enhance cognition has an outer layer that releases a nontoxic dye in water or water-alcohol solutions (alcoholic drinks) sufficient in color to show that the drink has been tampered with.

In another aspect of the invention, a formulation of oxytocin to enhance cognition has an outer layer that releases a nontoxic gelling agent in water or water-alcohol solutions sufficient to thicken or solidify the drink to show it has been tampered with.

In one embodiment, the composition is that comprising bupropion, comprising bupropion in a dosage range of 100-450 mg qd; comprising bupropion in a dosage range of 200-450 mg qd; comprising bupropion in a dosage range of 100-300 mg qd; comprising bupropion in a dosage range of 225-300 mg qd; comprising bupropion in a dosage range of 100-275 mg qd; or comprising bupropion in a dosage range of 200-275 mg qd; comprising bupropion in a dosage range of XX-YY mg qd, wherein XX is an integer between 5 and 400 and YY is an integer between 50 and 450.

In one embodiment, the composition is that comprising trazodone, comprising trazodone in a dosage range of 25-450 mg qd; comprising trazodone in a dosage range of 75-150 mg qd; or comprising trazodone in a dosage range of 50-100 mg qd; comprising trazodone in a dosage range of XX-YY mg qd, wherein XX is an integer between 25 and 400 and YY is an integer between 50 and 450.

In one embodiment, the composition is that comprising oxytocin, comprising oxytocin in a dosage range of 4-400 International Units.

In one embodiment, the composition is that comprising bupropion and trazodone, comprising bupropion in a dosage range of 50-450 mg and trazodone in a dosage range of 25-450 mg; comprising bupropion in a dosage range of 200-450 mg and trazodone in a dosage range of 25-450 mg; comprising bupropion in a dosage range of 100-300 mg qd and comprising trazodone in a dosage range of 75-150 mg qd; comprising bupropion in a dosage range of 225-300 mg qd and comprising trazodone in a dosage range of 75-150 mg qd; comprising bupropion in a dosage range of 100-275 mg qd and comprising trazodone in a dosage range of 50-100 mg qd; or comprising bupropion in a dosage range of 200-275 mg qd and comprising trazodone in a dosage range of 50-100 mg qd.

In one embodiment, the composition is that comprising bupropion, trazodone, and oxytocin, comprising bupropion in a dosage range of 50-450 mg, trazodone in a dosage range of 25-450 mg, and oxytocin in a dose range of 4-400 International Units; comprising bupropion in a dosage range of 200-450 mg, trazodone in a dosage range of 25-450 mg, and oxytocin in a dose range of 4-400 International Units; comprising bupropion in a dosage range of 100-300 mg qd, comprising trazodone in a dosage range of 75-150 mg qd, and oxytocin in a dose range of 4-400 International Units qd; comprising bupropion in a dosage range of 225-300 mg qd, comprising trazodone in a dosage range of 75-150 mg qd, and oxytocin in a dose range of 4-400 International Units qd; comprising bupropion in a dosage range of 100-275 mg qd, comprising trazodone in a dosage range of 50-100 mg qd, and comprising oxytocin in a dose range of 4-400 International Units qd; or comprising bupropion in a dosage range of 200-275 mg qd, comprising trazodone in a dosage range of 50-100 mg qd, and comprising oxytocin in a dose range of 4-400 International Units.

In one embodiment, the composition is that comprising bupropion and oxytocin, comprising bupropion in a dosage range of 50-450 mg and oxytocin in a dosage range of 4-400 International Units; comprising bupropion in a dosage range of 200-450 mg and oxytocin in a dosage range of 4-400 International Units; comprising bupropion in a dosage range of 100-300 mg qd and comprising oxytocin in a dosage range of 4-400 International Units qd; comprising bupropion in a dosage range of 225-300 mg qd and comprising oxytocin in a dosage range of 4-400 International Units qd; comprising bupropion in a dosage range of 100-275 mg qd and comprising oxytocin in a dosage range of 4-400 International Units qd; or comprising bupropion in a dosage range of 200-275 mg qd and comprising oxytocin in a dosage range of 4-400 International Units qd.

In one embodiment, the composition is that comprising oxytocin and trazodone, comprising oxytocin in a dosage range of 4-400 International Units and trazodone in a dosage range of 25-450 mg; comprising oxytocin in a dosage range of 4-400 International Units qd and comprising trazodone in a dosage range of 75-150 mg qd; or comprising oxytocin in a dosage range of 4-400 International Units qd and comprising trazodone in a dosage range of 50-100 mg qd.

In one aspect, the invention provides a method of making a composition comprising combining a 5-$HT_{1A}$ agonist/5-$HT_{2A}$ antagonist, a norepinephrine-dopamine reuptake inhibitor, and a pharmaceutically acceptable carrier. In one aspect, the invention provides a method of making a composition comprising combining a 5-$HT_{1A}$ receptor agonist, a 5-$HT_{2A}$ antagonist, and a pharmaceutically acceptable carrier. In one aspect, the invention provides a method of making a composition comprising combining a 5-$HT_{1A}$ receptor agonist, and a pharmaceutically acceptable carrier. In one aspect, the invention provides a method of making a composition comprising combining a 5-$HT_{1A}$ receptor agonist, 5-$HT_{2A}$ receptor antagonist, and/or 5-$HT_{2C}$ receptor antagonist, and a pharmaceutically acceptable carrier.

In one aspect, the invention provides a method of making a composition comprising combining a 5-$HT_{1A}$ agonist/5-$HT_{2A}$ antagonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, the invention provides a method of making a composition comprising combining a 5-$HT_{1A}$ receptor agonist, a 5-$HT_{2A}$ antagonist, and a pharmaceutically acceptable carrier. In one aspect, the invention provides a method of making a composition comprising combining a 5-$HT_{1A}$ receptor agonist, and a pharmaceutically acceptable carrier. In one aspect, the invention provides a method of making a composition comprising combining a 5-$HT_{1A}$ receptor agonist, 5-$HT_{2A}$ receptor antagonist, and/or 5-$HT_{2C}$ receptor antagonist, and a pharmaceutically acceptable carrier.

In one aspect, the invention provides a method of making a composition comprising combining a 5-$HT_{1A}$ agonist/5-$HT_{2A}$ antagonist, a norepinephrine-dopamine reuptake inhibitor, a 5-$HT_{2C}$ agonist (e.g., lorcaserin, vabicaserin, PRX-00933, YM348, metachlorophenylpiperazine, and mCPP), and a pharmaceutically acceptable carrier. In one aspect, the invention provides a method of making a composition comprising combining a 5-$HT_{1A}$ receptor agonist, a 5-$HT_{2A}$ antagonist, and a pharmaceutically acceptable carrier. In one aspect, the invention provides a method of making a composition comprising combining a 5-$HT_{1A}$ receptor agonist, and a pharmaceutically acceptable carrier. In one aspect, the invention provides a method of making a composition comprising combining a 5-$HT_{1A}$ receptor agonist, 5-$HT_{2A}$ receptor antagonist, and/or 5-$HT_{2C}$ receptor antagonist, and a pharmaceutically acceptable carrier.

In one aspect, the invention provides a method of making a composition comprising combining a 5-$HT_{1A}$ agonist/5-$HT_{2A}$ antagonist, a norepinephrine-dopamine reuptake inhibitor, a 5-$HT_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier. In one aspect, the invention provides a method of making a composition comprising combining a 5-$HT_{1A}$ receptor agonist, a 5-$HT_{2A}$ antagonist, and a pharmaceutically acceptable carrier. In one aspect, the invention provides a method of making a composition comprising combining a 5-$HT_{1A}$ receptor agonist, and a pharmaceutically acceptable carrier. In one aspect, the invention provides a method of making a composition comprising combining a 5-$HT_{1A}$ receptor agonist, 5-$HT_{2A}$ receptor antagonist, and/or 5-$HT_{2C}$ receptor antagonist, and a pharmaceutically acceptable carrier.

In one aspect, the method of making a composition comprises combining a 5-$HT_{1A}$ receptor agonist, a norepinephrine-dopamine reuptake inhibitor and a pharmaceutically acceptable carrier such that the composition comprises a range of 25-450 mg of a 5-$HT_{1A}$ receptor agonist. In another aspect, the invention provides a method of making a composition comprising combining a 5-$HT_{1A}$ receptor agonist, 5-$HT_{2A}$ receptor antagonist, and/or 5-$HT_{2C}$ receptor antagonist and a pharmaceutically acceptable carrier such that the composition comprises a range of 25-450 mg of a 5-$HT_{2A}$ antagonist and a norepinephrine-dopamine reuptake inhibitor.

In one aspect, the method of making a composition comprises combining a 5-$HT_{1A}$ receptor agonist, a norepinephrine-dopamine reuptake inhibitor, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-$HT_{1A}$ receptor agonist. In another aspect, the invention provides a method of making a composition comprising combining a 5-$HT_{1A}$ receptor agonist, 5-$HT_{2A}$ receptor antagonist, and/or 5-$HT_{2C}$ receptor antagonist and a pharmaceutically acceptable carrier such that the composition comprises a range of 25-450 mg of a 5-$HT_{2A}$ antagonist and a norepinephrine-dopamine reuptake inhibitor.

In one aspect, the method of making a composition comprises combining a 5-HT$_{1A}$ receptor agonist, a norepinephrine-dopamine reuptake inhibitor, a 5-HT$_{2C}$ agonist (e.g., lorcaserin, vabicaserin, PRX-00933, YM348, metachlorophenylpiperazine, and mCPP), and a pharmaceutically acceptable carrier such that the composition comprises a range of 25-450 mg of a 5-HT$_{1A}$ receptor agonist. In another aspect, the invention provides a method of making a composition comprising combining a 5-HT$_{1A}$ receptor agonist, 5-HT$_{2A}$ receptor antagonist, and/or 5-HT$_{2C}$ receptor antagonist and a pharmaceutically acceptable carrier such that the composition comprises a range of 25-450 mg of a 5-HT$_{2A}$ antagonist and a norepinephrine-dopamine reuptake inhibitor.

In one aspect, the method of making a composition comprises combining a 5-HT$_{1A}$ receptor agonist, a norepinephrine-dopamine reuptake inhibitor, a 5-HT$_{2C}$ agonist (e.g., lorcaserin, vabicaserin, PRX-00933, YM348, metachlorophenylpiperazine, and mCPP), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-HT$_{1A}$ receptor agonist. In another aspect, the invention provides a method of making a composition comprising combining a 5-HT$_{1A}$ receptor agonist, 5-HT$_{2A}$ receptor antagonist, and/or 5-HT$_{2C}$ receptor antagonist and a pharmaceutically acceptable carrier such that the composition comprises a range of 25-450 mg of a 5-HT$_{2A}$ antagonist and a norepinephrine-dopamine reuptake inhibitor.

In one embodiment, the method comprises combining bupropion, trazodone, and a pharmaceutically acceptable carrier.

In one embodiment, the method comprises combining bupropion, trazodone, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier.

In one embodiment, the method comprises combining bupropion, trazodone, a 5-HT$_{2C}$ agonist (e.g., lorcaserin, vabicaserin, PRX-00933, YM348, metachlorophenylpiperazine, and mCPP), and a pharmaceutically acceptable carrier.

In one embodiment, the method comprises combining bupropion, trazodone, a 5-HT$_{2C}$ agonist (e.g., lorcaserin, vabicaserin, PRX-00933, YM348, metachlorophenylpiperazine, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and mCPP), and a pharmaceutically acceptable carrier.

In one aspect, the method of making a composition comprises combining a 5-HT$_{1A}$ receptor agonist, a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist (e.g., trazodone, nefazodone, mirtazapine, flibanserin) and a pharmaceutically acceptable carrier such that the composition comprises a range of 25-450 mg of a 5-HT$_{2A}$ antagonist, a norepinephrine-dopamine reuptake inhibitor (e.g., bupropion), and an oxytocin receptor (OXTR) agonist (e.g., carbetocin, oxytocin, Syntocinon®).

In one aspect, the method of making a composition comprises combining a 5-HT$_{1A}$ receptor agonist, a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines) and a pharmaceutically acceptable carrier such that the composition comprises a range of 25-450 mg of a 5-HT$_{2A}$ antagonist, a norepinephrine-dopamine reuptake inhibitor (e.g., bupropion), and an oxytocin receptor (OXTR) agonist (e.g., carbetocin, oxytocin, Syntocinon®).

In one aspect, the method of making a composition comprises combining a 5-HT$_{1A}$ receptor agonist, a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines) and a pharmaceutically acceptable carrier such that the composition comprises a range of 25-450 mg of a 5-HT$_{2A}$ antagonist, a norepinephrine-dopamine reuptake inhibitor (e.g., bupropion), and an oxytocin receptor (OXTR) agonist (e.g., carbetocin, oxytocin, Syntocinon®).

In one aspect, the method of making a composition comprises combining a 5-HT$_{1A}$ receptor agonist, a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines) and a pharmaceutically acceptable carrier such that the composition comprises a range of 25-450 mg of a 5-HT$_{2A}$ antagonist, a norepinephrine-dopamine reuptake inhibitor (e.g., bupropion), and an oxytocin receptor (OXTR) agonist (e.g., carbetocin, oxytocin, Syntocinon®).

In one aspect, the method of making a composition comprises combining a 5-HT$_{1A}$ receptor agonist, a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimido-azepines) and a pharmaceutically acceptable carrier such that the composition comprises a range of 25-450 mg of a 5-HT$_{2A}$ antagonist, a norepinephrine-dopamine reuptake inhibitor (e.g., bupropion), and an oxytocin receptor (OXTR) agonist (e.g., carbetocin, oxytocin, Syntocinon®).

In one embodiment, the method comprises combining bupropion, trazodone, oxytocin (Syntocinon®), and a pharmaceutically acceptable carrier.

In one aspect, the method of making a composition comprises combining a 5-HT$_{2A}$ receptor antagonist (e.g., trazodone, nefazodone, mirtazapine, flibanserin), a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 50-450 mg of a norepinephrine-dopamine reuptake inhibitor, a 5-HT$_{2A}$ antagonist, and an oxytocin receptor (OXTR) agonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 50-450 mg of a norepinephrine-dopamine reuptake inhibitor, a 5-HT$_{2A}$ antagonist, and an oxytocin receptor (OXTR) agonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 50-450 mg of a norepinephrine-dopamine reuptake inhibitor, a 5-HT$_{2A}$ antagonist, and an oxytocin receptor (OXTR) agonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 50-450 mg of a norepinephrine-dopamine reuptake inhibitor, a 5-HT$_{2A}$ antagonist, and an oxytocin receptor (OXTR) agonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 50-450 mg of a norepinephrine-dopamine reuptake inhibitor, a 5-HT$_{2A}$ antagonist, and an oxytocin receptor (OXTR) agonist.

In one embodiment, the method comprises combining bupropion, trazodone, oxytocin, and a pharmaceutically acceptable carrier.

In one aspect, the method of making a composition comprises combining a 5-HT$_{2A}$ receptor antagonist (e.g., trazodone, nefazodone, mirtazapine, flibanserin), a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 4-400 International Units of an oxytocin receptor (OXTR) agonist, a norepinephrine-dopamine reuptake inhibitor, and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripirazole, and the general class of 2-alkyl-4-aryl-tetrahydro-pyrimidoazepines), a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 4-400 International Units of an oxytocin receptor (OXTR) agonist, a norepinephrine-dopamine reuptake inhibitor, and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist, a norepinephrine-dopamine reuptake inhibitor, and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 4-400 International Units of an oxytocin receptor (OXTR) agonist, a norepinephrine-dopamine reuptake inhibitor, and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist, a norepinephrine-dopamine reuptake inhibitor, and a 5-HT$_{2A}$ antagonist.

In one embodiment, the method comprises combining bupropion, trazodone, oxytocin, and a pharmaceutically acceptable carrier.

In one aspect, the method of making a composition comprises combining a 5-HT$_{1A}$ receptor agonist (e.g., trazodone, nefazodone, mirtazapine, flibanserin), an oxytocin receptor (OXTR) agonist (e.g., carbetocin, oxytocin, Syntocinon®), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist and a pharmaceutically acceptable carrier such that the composition comprises a range of 25-450 mg of a 5-HT$_{2A}$ antagonist and an oxytocin receptor (OXTR) agonist.

In one aspect, the method of making a composition comprises combining a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), an oxytocin receptor (OXTR) agonist (e.g., carbetocin, oxytocin, Syntocinon®), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist and a pharmaceutically acceptable carrier such that the composition comprises a range of 25-450 mg of a 5-HT$_{2A}$ antagonist and an oxytocin receptor (OXTR) agonist.

In one aspect, the method of making a composition comprises combining a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist and a pharmaceutically acceptable carrier such that the composition comprises a range of 25-450 mg of a 5-HT$_{2A}$ antagonist and an oxytocin receptor (OXTR) agonist.

In one aspect, the method of making a composition comprises combining a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist and a pharmaceutically acceptable carrier such that the composition comprises a range of 25-450 mg of a 5-HT$_{2A}$ antagonist and an oxytocin receptor (OXTR) agonist.

In one aspect, the method of making a composition comprises combining a 5-HT$_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimidoazepines), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 25-450 mg of a 5-HT$_{1A}$ receptor agonist. In another aspect, the method of making comprises combining a 5-HT$_{1A}$ agonist/5-HT$_{2A}$ antagonist and a pharmaceutically acceptable carrier such that the composition comprises a range of 25-450 mg of a 5-HT$_{2A}$ antagonist and an oxytocin receptor (OXTR) agonist.

In one embodiment, the method comprises combining trazodone, oxytocin, and a pharmaceutically acceptable carrier.

In one aspect, the method of making a composition comprises combining a 5-HT$_{2A}$ receptor antagonist (e.g., trazodone, nefazodone, mirtazapine, flibanserin), an oxytocin receptor (OXTR) agonist (e.g., carbetocin, oxytocin, Syntocinon®), and a pharmaceutically acceptable carrier such that the composition comprises a range of 4-400 International Units of an oxytocin receptor (OXTR) agonist and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimidoazepines), an oxytocin receptor (OXTR) agonist (e.g., carbetocin, oxytocin, Syntocinon®), and a pharmaceutically acceptable carrier such that the composition comprises a range of 4-400 International Units of an oxytocin receptor (OXTR) agonist and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimidoazepines), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimidoazepines), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 4-400 International Units of an oxytocin receptor (OXTR) agonist and a 5-HT$_{2A}$ antagonist.

In one aspect, the method of making a composition comprises combining a 5-HT$_{2A}$ receptor antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimidoazepines), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist and a 5-HT$_{2A}$ antagonist.

In one embodiment, the method comprises combining trazodone, oxytocin, and a pharmaceutically acceptable carrier.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 50-450 mg of a norepinephrine-dopamine reuptake inhibitor and an oxytocin receptor (OXTR) agonist.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 50-450 mg of a norepinephrine-dopamine reuptake inhibitor and an oxytocin receptor (OXTR) agonist.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 50-450 mg of a norepinephrine-dopamine reuptake inhibitor and an oxytocin receptor (OXTR) agonist.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 50-450 mg of a norepinephrine-dopamine reuptake inhibitor and an oxytocin receptor (OXTR) agonist.

In one embodiment, the method comprises combining bupropion, oxytocin, and a pharmaceutically acceptable carrier.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), and a pharmaceutically acceptable carrier such that the composition comprises a range of 4-400 International Units of an oxytocin receptor (OXTR) agonist and a norepinephrine-dopamine reuptake inhibitor.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist and a norepinephrine-dopamine reuptake inhibitor.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), and a pharmaceutically acceptable carrier such that the composition comprises a range of 4-400 International Units of an oxytocin receptor (OXTR) agonist and a norepinephrine-dopamine reuptake inhibitor.

In one aspect, the method of making a composition comprises combining a norepinephrine-dopamine reuptake inhibitor (e.g., bupropion), an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a pharmaceutically acceptable carrier such that the composition comprises a range of 4-400 International Units of an oxytocin receptor (OXTR) agonist and a norepinephrine-dopamine reuptake inhibitor.

In one embodiment, the method comprises combining bupropion, oxytocin, and a pharmaceutically acceptable carrier.

In one aspect, the invention provides a kit comprising a composition delineated herein and a label providing instructions for administration of the composition to a subject for treating or ameliorating sexual disorders or symptoms thereof in the subject.

In one aspect, the invention provides a kit comprising a composition delineated herein and a label providing instructions for administration of the composition to a subject for treating or ameliorating cognitive disorders or symptoms thereof in the subject.

In one aspect, the invention provides a kit comprising a composition delineated herein and a label providing instructions for administration of the composition to a subject for enhancing cognition in the subject.

In another aspect, the invention provides a method of treating sexual disorders in a subject comprising administering to the subject a 5-HT$_{1A}$ receptor agonist, and a 5-HT$_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating sexual disorders in a subject comprising administering to the subject a 5-HT$_{1A}$ receptor agonist, a 5-HT$_{2A}$ antagonist, and ther non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*). The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating sexual disorders in a subject comprising administering to the subject a 5-HT$_{1A}$ receptor agonist, a 5-HT$_{2A}$ antagonist, and a 5-HT$_{2C}$ agonist (e.g., lorcaserin, vabicaserin, PRX-00933, YM348, metachlorophenylpiperazine). The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating sexual disorders in a subject comprising administering to the subject a 5-HT$_{1A}$ receptor agonist, a 5-HT$_{2A}$ antagonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-HT$_{2C}$ agonist (e.g., lorcaserin, vabicaserin, PRX-00933, YM348, metachlorophenylpiperazine). The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another embodiment, the invention provides a method of treating a subject suffering from or susceptible to a sexual disorder comprising administering to a subject in need thereof a therapeutically effective amount of a composition comprising any one of a 5-HT$_{2A}$ antagonist, a norepinephrine-dopamine reuptake inhibitor (e.g., bupropion), a 5-HT$_{1A}$ receptor agonist, an oxytocin receptor (OXTR) agonist (e.g., carbetocin, oxytocin, Syntocinon®), an endocrine active agent, or any combination thereof and a pharmaceutically acceptable carrier.

In another embodiment, the invention provides a method of treating a subject suffering from or susceptible to a sexual disorder comprising administering to a subject in need thereof a therapeutically effective amount of a composition comprising any one of a 5-HT$_{2A}$ antagonist, a norepinephrine-dopamine reuptake inhibitor (e.g., bupropion), a 5-HT$_{1A}$ receptor agonist, an oxytocin receptor (OXTR) agonist (e.g., carbetocin, oxytocin, Syntocinon®), a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof and a pharmaceutically acceptable carrier.

In another aspect, the invention provides a method of treating sexual disorders in a subject comprising administering to the subject a therapeutically effective amount of any one of a 5-HT$_{2A}$ antagonist, a norepinephrine-dopamine reuptake inhibitor (e.g., bupropion), a 5-HT$_{1A}$ receptor agonist, an oxytocin receptor (OXTR) agonist (e.g., carbetocin, oxytocin, Syntocinon®), an endocrine active agent, or any combination thereof.

In another aspect, the invention provides a method of treating sexual disorders in a subject comprising administering to the subject a therapeutically effective amount of any one of a 5-HT$_{2A}$ antagonist, a norepinephrine-dopamine reuptake inhibitor (e.g., bupropion), a 5-HT$_{1A}$ receptor agonist, an oxytocin receptor (OXTR) agonist (e.g., carbetocin, oxytocin, Syntocinon®), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), a 5-HT$_{2C}$ agonist (e.g., lorcaserin, vabicaserin, PRX-00933, YM348, metachlorophenylpiperazine), an endocrine active agent, or any combination thereof.

In another aspect, the invention provides a method of treating cognitive disorders in a subject comprising administering to the subject a 5-HT$_{1A}$ receptor agonist, and a 5-HT$_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating cognitive disorders in a subject comprising administering to the subject a 5-HT$_{1A}$ receptor agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-HT$_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating cognitive disorders in a subject comprising administering to the subject a 5-HT$_{1A}$ receptor agonist, a 5-HT$_{2C}$ agonist (e.g., lorcaserin, vabicaserin, PRX-00933, YM348, metachlorophenylpiperazine), and a 5-HT$_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of treating cognitive disorders in a subject comprising administering to the subject a 5-HT$_{1A}$ receptor agonist, a 5-HT$_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-HT$_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another embodiment, the invention provides a method of treating a subject suffering from or susceptible to a cognitive disorder comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), an endocrine active agent, or any combination thereof and a pharmaceutically acceptable carrier.

In another embodiment, the invention provides a method of treating a subject suffering from or susceptible to a cognitive disorder comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof and a pharmaceutically acceptable carrier.

In another aspect, the invention provides a method of treating cognitive disorders in a subject comprising administering to the subject a therapeutically effective amount of any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), an endocrine active agent, or any combination thereof.

In another aspect, the invention provides a method of treating cognitive disorders in a subject comprising administering to the subject a therapeutically effective amount of any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof.

In another aspect, the invention provides a method of enhancing cognition in a subject comprising administering to the subject a 5-$HT_{1A}$ receptor agonist, and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of enhancing cognition in a subject comprising administering to the subject a 5-$HT_{1A}$ receptor agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of enhancing cognition in a subject comprising administering to the subject a 5-$HT_{1A}$ receptor agonist, a 5-$HT_{2C}$ agonist (e.g., lorcaserin, vabicaserin, PRX-00933, YM348, metachlorophenylpiperazine), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of enhancing cognition in a subject comprising administering to the subject a 5-$HT_{1A}$ receptor agonist, a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another embodiment, the invention provides a method of enhancing cognition comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), an endocrine active agent, or any combination thereof and a pharmaceutically acceptable carrier.

In another embodiment, the invention provides a method of enhancing cognition comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof and a pharmaceutically acceptable carrier.

In another aspect, the invention provides a method of enhancing cognition in a subject comprising administering to the subject a therapeutically effective amount of any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), an endocrine active agent, or any combination thereof.

In another aspect, the invention provides a method of enhancing cognition in a subject comprising administering to the subject a therapeutically effective amount of any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof.

In another aspect, the invention provides a method of relieving depression in a subject comprising administering to the subject a 5-$HT_{1A}$ receptor agonist, and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of relieving depression in a subject comprising administering to the subject a 5-$HT_{1A}$ receptor agonist, other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of relieving depression in a subject comprising administering to the subject a 5-$HT_{1A}$ receptor agonist, a 5-$HT_{2C}$ agonist (e.g., lorcaserin, vabicaserin, PRX-00933, YM348, metachlorophenylpiperazine), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another aspect, the invention provides a method of relieving depression in a subject comprising administering to the subject a 5-$HT_{1A}$ receptor agonist, a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), and a 5-$HT_{2A}$ antagonist. The methods herein can further comprise those wherein the subject is identified as in need of such treatment, and those wherein the subject is treated upon administration of the compounds and/or compositions herein. The methods can include those wherein the subject has not previously been administered the compounds and/or compositions herein, or wherein the subject has not previously been administered the compounds and/or compositions herein at the stated dosage levels or administration regimens.

In another embodiment, the invention provides a method of relieving depression comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), an endocrine active agent, or any combination thereof and a pharmaceutically acceptable carrier.

In another embodiment, the invention provides a method of relieving depression comprising administering to a subject in need thereof a therapeutically effective amount of a composition comprising any one of a 5-$HT_{2A}$ antagonist, a norepinephrine-dopamine reuptake inhibitor (e.g., bupropion), a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, *ginkgo biloba*), an endocrine active agent, or any combination thereof and a pharmaceutically acceptable carrier.

In another aspect, the invention provides a method of relieving depression in a subject comprising administering to the subject a therapeutically effective amount of any one of a 5-$HT_{2A}$ antagonist, a norepinephrine-dopamine reuptake inhibitor, a 5-$HT_{1A}$ receptor agonist, an oxytocin receptor (OXTR) agonist (e.g., carbetocin, oxytocin, Syntocinon®), an endocrine active agent, or any combination thereof.

In another aspect, the invention provides a method of relieving depression in a subject comprising administering to the subject a therapeutically effective amount of any one of a 5-$HT_{2A}$ antagonist, a norepinephrine-dopamine reuptake inhibitor, a 5-$HT_{1A}$ receptor agonist, an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), an endocrine active agent, or any combination thereof.

In aspects the endocrine agent is testosterone, which can be in an amount of a dosage range of 25 to 1000 mg per day in men or 150 to 300 micrograms per day in women.

In aspects, the subject is that wherein the subject is not being treated with a selective serotonin reuptake inhibitor (SSRI) agent.

In aspects, the subject is that wherein the subject is being treated with a selective serotonin reuptake inhibitor (SSRI) agent.

In aspects, the subject is that wherein the subject is identified as having selective serotonin reuptake inhibitor (SSRI) agent induced sexual disorders.

In aspects, the subject is that wherein the subject is being treated with a PDE-5 inhibitor compound (i.e., sildenafil, tadalafil, and the like).

In aspects, the subject is that wherein the subject is not concurrently being treated with a PDE-5 inhibitor compound (i.e., sildenafil, tadalafil, and the like).

In aspects, the subject is that wherein the subject is being treated with an endocrine agent (e.g., testosterone).

In aspects, the subject is that wherein the subject is not concurrently being treated with an endocrine agent (e.g., testosterone).

In another aspect, the methods herein comprise taking a sample (i.e., fluid, blood, urine, saliva, tissue, etc.) and assessing a biological marker (i.e., liver enzymes, CYP3A4, and/or a genetic marker of the transport, receptor type, receptor density, receptor affinity, metabolism, or activity of serotonin, serotonin 1A or 2A subtype, dopamine, or a receptor subtype of dopamine) to measure health status of the subject either prior to, during or after administration of the compositions herein.

DETAILED DESCRIPTION OF THE INVENTION

The present inventors have now discovered a therapeutic strategy that addresses sexual disorders, cognitive disorders, or offers cognition enhancement in a subject.

The present invention relates, at least in part, to the discovery that a combination of a 5-$HT_{2A}$ antagonist (which is optionally a 5-$HT_{1A}$ receptor agonist) (e.g., trazodone, nefazodone, mirtazapine, flibanserin), a norepinephrine-dopamine reuptake inhibitor (e.g., bupropion), and oxytocin receptor (OXTR) agonist (e.g., carbetocin, oxytocin, Syntocinon®), (and optionally an endocrine active agent) provides unexpected superior and synergistic results in addressing sexual disorders, cognitive disorders, or offers cognition enhancement in a subject.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, buccal, sublingual, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their minor image partner.

The term "diastereomers" refers to stereoisomers with two or more centers of dissymmetry and whose molecules are not minor images of one another.

The term "effective amount" includes an amount effective, at dosages and for periods of time necessary, to achieve the desired result, e.g., sufficient to treat a sexual disorder or hypoactive sexual desire disorder in a subject. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments.

In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment. Administration regimens herein where designated are in accordance with the following abbreviations: SID or QD=Once a day; BID=Twice a day, TID=Three times a day; QID=Four times a day; q.h.s=every night.

The term "enantiomers" refers to two stereoisomers of a compound which are non-superimposable minor images of one another. An equimolar mixture of two enantiomers is called a "racemic mixture" or a "racemate." The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., the alteration in sexual disorder or hypoactive sexual desire disorder and/or symptoms thereof in a subject such that a desired end result is achieved, e.g., a therapeutic result.

The term "obtaining" as in "obtaining a compound useful in treating sexual disorder or hypoactive sexual desire disorder" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a sexual disorder.

The language "reduced toxicity" is intended to include a reduction in any undesired side effect elicited by a compound of the invention when administered in vivo e.g., formulating bupropion, by itself a mild stimulant, with trazodone, by itself a moderate sedative, in the proprietary ratio of Lorexys will neutralize the main side effects of each of the two drugs.

The term "subject" includes organisms which are capable of suffering from a sexual disorder or who could otherwise benefit from the administration of a compound or composition of the invention, such as human (male or female) and non-human animals (male or female). Preferred humans include human patients suffering from or prone to suffering from sexual disorder or hypoactive sexual desire disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a sexual disorder or hypoactive sexual desire disorder" is meant to include subjects at risk of developing sexual disorder or hypoactive sexual desire disorder, e.g., subjects previously diagnosed as having or having a family or medical history of sexual disorder or hypoactive sexual desire disorder, and the like.

The phrases "systemic administration, "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in modulating sexual disorder or hypoactive sexual desire disorder and/or symptoms of sexual disorder or hypoactive sexual desire disorder, or in improving the patient (either objectively or subjectively according to the patient or health care provider) beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides compounds capable of modulating sexual disorder or hypoactive sexual desire disorder in a subject. Such compounds include a 5-$HT_{2A}$ antagonist (e.g., trazodone, nefazodone, mirtazapine, flibanserin), a 5-$HT_{1A}$ receptor agonist (e.g., trazodone, nefazodone, mirtazapine, flibanserin), a norepinephrine-dopamine reuptake inhibitor (e.g., bupropion), an oxytocin receptor (OXTR) agonist (e.g., carbetocin, oxytocin, Syntocinon®), and an endocrine active agent. Compositions of the invention further include a pharmaceutically acceptable carrier.

In one aspect, the invention provides compounds capable of modulating sexual disorder or hypoactive sexual desire disorder in a subject. Such compounds include a 5-$HT_{2A}$ antagonist (e.g., trazodone, nefazodone, mirtazapine, flibanserin), a 5-$HT_{1A}$ receptor agonist (e.g., trazodone, nefazodone, mirtazapine, flibanserin), a norepinephrine-dopamine reuptake inhibitor (e.g., bupropion), an oxytocin receptor (OXTR) agonist (e.g., carbetocin, oxytocin, Syntocinon®), a 5-$HT_{2C}$ agonist (e.g., lorcaserin, vabicaserin, PRX-00933, YM348, metachlorophenylpiperazine), other non-abusable agents (agents not scheduled by the DEA) that augment dopamine and/or norepinephrine in the brain, e.g., atomoxetine, reboxetine, amedalin, CP-39,332, daledalin, edivoxetine, esreboxetine, lortalamine, mazindol, nisoxetine, talopram, talsupram, tandamine, viloxazine, maprotiline, ciclazindol, manifaxine, radafaxine, tapentadol, teniloxazine, St. John's wort, ginkgo biloba), and an endocrine active agent. Compositions of the invention further include a pharmaceutically acceptable carrier.

The compounds delineated herein include a 5-$HT_{2A}$ antagonist (e.g., trazodone, nefazodone, mirtazapine, flibanserin), that is a compound that demonstrates antagonistic activity against the 5-$HT_{2A}$ receptor; a norepinephrine-dopamine reuptake inhibitor (e.g., bupropion); that is a compound that exhibits inhibition activity in norepinephrine-dopamine reuptake; a 5-$HT_{1A}$ receptor agonist (e.g., trazodone, nefazodone, mirtazapine, flibanserin), that is a compound that demonstrates agonist activity against the 5-$HT_{1A}$ receptor; an oxytocin receptor (OXTR) agonist (e.g., carbetocin, oxytocin, Syntocinon®), that is a compound that demonstrates agonistic activity against the oxytocin receptor; and an endocrine active agent, that is an agent that is active in modulating the endocrine system.

The compounds delineated herein include a 5-$HT_{2A}$ antagonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydro-pyrimido-azepines), that is a compound that demonstrates antagonistic activity against the 5-$HT_{2A}$ receptor; a norepinephrine-dopamine reuptake inhibitor (e.g., bupropion); that is a compound that exhibits inhibition activity in norepinephrine-dopamine reuptake; a 5-$HT_{1A}$ receptor agonist (e.g., trazodone, nefazodone, mirtazapine, flibanserin, ketanserin, ritanserin, clozapine, olanzapine, quetiapine, risperidone, asenapine, MDL-100,907, cyproheptadine, aripiprazole, and the general class of 2-alkyl-4-aryl-tetrahydropyrimido-azepines), that is a compound that demonstrates agonist activity against the 5-$HT_{1A}$ receptor; an oxytocin receptor (OXTR) agonist (e.g., carbetocin, oxytocin, Syntocinon®), that is a compound that demonstrates agonistic activity against the oxytocin receptor; and an endocrine active agent, that is an agent that is active in modulating the endocrine system.

In one embodiment, the invention provides a compound (e.g., a compound herein) capable of modulating sexual disorder or hypoactive sexual desire disorder; and pharmaceutically acceptable esters, salts, isomers and prodrugs thereof.

In another embodiment, the invention provides a compound (e.g., a compound herein) capable of modulating cognition disorder; and pharmaceutically acceptable esters, salts, isomers and prodrugs thereof.

In another embodiment, the invention provides a compound (e.g., a compound herein) capable of enhancing cognition; and pharmaceutically acceptable esters, salts, isomers and prodrugs thereof.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

In one embodiment, the invention provides methods of treating a disease or disorder in a subject comprising administering to the subject a composition delineated herein. In one embodiment, the invention provides methods of treating sexual disorder in a subject comprising administering to the subject a composition delineated herein. In certain embodiments, the subject is a mammal, e.g., a primate, e.g., a human. In aspect, the disease, disorder or symptom thereof in which the compounds, compositions, and methods of treatment relate to is one described in the Diagnostic and Statistical Manual of Mental Disorders 4$^{th}$ edition—Text Revision, (DSM-I-TRV), American Psychiatric Association.

In certain embodiments, the methods of the invention include administering to a subject a therapeutically effective amount of a compound of the invention in combination with another pharmaceutically active compound. Examples of pharmaceutically active compounds include compounds known to treat sexual disorder in a subject. Other pharmaceutically active compounds that may be used can be found in *Harrison's Principles of Internal Medicine,* Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

Determination of a therapeutically effective sexual disorder effective amount, a prophylactically effective sexual disorder or hypoactive sexual desire disorder amount of the compound of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective sexual disorder or hypoactive sexual desire disorder amount or dose, and the prophylactically effective sexual disorder or hypoactive sexual desire disorder amount or dose, a number of factors are considered by the attending clinician, including, but not limited to: the specific sexual disorder or hypoactive sexual desire disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

The dosage administration can be in a single dosage form or multiple dosage forms. The dosages can be administered concurrently, simultaneously, or sequentially. The dosages can be a single dosage immediately prior to sexual activity, or can be one or more doses daily without regard to timing prior to sexual activity. Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

The identification of those patients who are in need of prophylactic treatment for sexual disorder or hypoactive sexual desire disorder is well within the ability and knowledge of one skilled in the art. Certain of the methods for identification of patients which are at risk of developing sexual disorder or hypoactive sexual desire disorder which can be treated by the subject method are appreciated in the medical arts, such as family history, and the presence of risk factors associated with the development of that disease state in the subject patient (e.g., use of antidepressant drugs, hormonal contraceptives, antihormonal and/or cytotoxic chemotherapies, sedatives, antipsychotic drugs, antiepileptic drugs, mood stabilizer drugs, opioid drugs, alcohol, or narcotic drugs). A clinician skilled in the art can readily identify such candidate patients, by the use of, for example, clinical tests, physical examination and medical/family history.

As used herein, "obtaining a biological sample from a subject," includes obtaining a sample for use in the methods described herein. A biological sample is described above.

In another aspect, a compound of the invention is packaged in a therapeutically effective amount with a pharmaceutically acceptable carrier or diluent. The composition may be formulated for treating a subject suffering from or susceptible to a sexual disorder or hypoactive sexual desire disorder, and packaged with instructions to treat a subject suffering from or susceptible to a sexual disorder or hypoactive sexual desire disorder.

The subject may be at risk of a sexual disorder or hypoactive sexual desire disorder, may be exhibiting symptoms of a sexual disorder or hypoactive sexual desire disorder, may be susceptible to a sexual disorder or hypoactive sexual desire disorder and/or may have been diagnosed with a sexual desire disorder.

If the modulation of the status indicates that the subject may have a favorable clinical response to the treatment, the subject may be treated with the compound. For example, the subject can be administered therapeutically effective dose or doses of the compound.

Kits of the invention include kits for treating a sexual disorder or hypoactive sexual desire disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. In aspects, the kits (and methods of using them) comprise instructions indicating that the compositions and/or treatment methods are contraindicated for (or not to be administered to) subjects that: (i) require and/or are taking CYP3A4, CYP 2B6-, or CYP 2D6-metabolized drugs; (ii) take any sex hormone other than an approved hormonal contraceptive; (iii) drink more than one alcoholic drink per day (e.g., 12-oz beer, 4-oz wine, etc).

Alternatively, the effects of compound of the invention can be characterized in vivo using animals models.

In another embodiment, the invention provides methods of treating cognitive disorder in a subject comprising administering to the subject a composition delineated herein. In certain embodiments, the subject is a mammal, e.g., a primate, e.g., a human. In aspect, the disease, disorder or symptom thereof in which the compounds, compositions, and methods of treatment relate to is one described in the Diagnostic and Statistical Manual of Mental Disorders 4$^{th}$ edition—Text Revision, (DSM-I-TRV), American Psychiatric Association.

In certain embodiments, the methods of the invention include administering to a subject a therapeutically effective amount of a compound of the invention in combination with another pharmaceutically active compound. Examples of pharmaceutically active compounds include compounds known to treat cognitive disorder in a subject. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

Determination of a therapeutically effective cognitive disorder effective amount, a prophylactically effective cognitive disorder amount of the compound of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective cognitive disorder amount or dose, and the prophylactically effective cognitive disorder amount or dose, a number of factors are considered by the attending clinician, including, but not limited to: the specific cognitive disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

The dosage administration can be in a single dosage form or multiple dosage forms. The dosages can be administered concurrently, simultaneously, or sequentially. The dosages can be a single dosage, or can be one or more doses daily. Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

The identification of those patients who are in need of prophylactic treatment for cognitive disorder is well within the ability and knowledge of one skilled in the art. Certain of the methods for identification of patients which are at risk of developing cognitive disorder which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

As used herein, "obtaining a biological sample from a subject," includes obtaining a sample for use in the methods described herein. A biological sample is described above.

In another aspect, a compound of the invention is packaged in a therapeutically effective amount with a pharmaceutically acceptable carrier or diluent. The composition may be formulated for treating a subject suffering from or susceptible to a cognition disorder, and packaged with instructions to treat a subject suffering from or susceptible to a cognition disorder.

The subject may be at risk of a cognition disorder, may be exhibiting symptoms of a cognition disorder, may be susceptible to a cognitive disorder and/or may have been diagnosed with a cognition disorder.

If the modulation of the status indicates that the subject may have a favorable clinical response to the treatment, the subject may be treated with the compound. For example, the subject can be administered therapeutically effective dose or doses of the compound.

Kits of the invention include kits for treating a cognitive disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. In aspects, the kits (and methods of using them) comprise instructions indicating that the compositions and/or treatment methods are contraindicated for (or not to be administered to) subjects that: (i) require and/or are taking CYP3A4, CYP 2B6-, or CYP 2D6-metabolized drugs; (ii) drink more than one alcoholic drink per day (e.g., 12-oz beer, 4-oz wine, etc).

Alternatively, the effects of compound of the invention can be characterized in vivo using animals models.

In another embodiment, the invention provides methods of enhancing cognition in a subject comprising administering to the subject a composition delineated herein. In certain embodiments, the subject is a mammal, e.g., a primate, e.g., a human. In aspect, the disease, disorder or symptom thereof in which the compounds, compositions, and methods of treatment relate to is one described in the Diagnostic and Statistical Manual of Mental Disorders 4$^{th}$ edition—Text Revision, (DSM-I-TRV), American Psychiatric Association.

In certain embodiments, the methods of the invention include administering to a subject a therapeutically effective amount of a compound of the invention in combination with another pharmaceutically active compound. Examples of pharmaceutically active compounds include compounds known to enhance cognition in a subject. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

Determination of a therapeutically effective cognition enhancing effective amount, a prophylactically effective cognition enhancement amount of the compound of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective cognition enhancement amount or dose, and the prophylactically effective cognition enhancing amount or dose, a number of factors are considered by the attending clinician, including, but not limited to: the specific cognition enhancement needed; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

The dosage administration can be in a single dosage form or multiple dosage forms. The dosages can be administered concurrently, simultaneously, or sequentially. The dosages can be a single dosage, or can be one or more doses daily. Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

The identification of those patients who are in need of prophylactic treatment for cognition enhancement is well within the ability and knowledge of one skilled in the art. Certain of the methods for identification of patients which are at risk of needing cognition enhancement which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

As used herein, "obtaining a biological sample from a subject," includes obtaining a sample for use in the methods described herein. A biological sample is described above.

In another aspect, a compound of the invention is packaged in a therapeutically effective amount with a pharmaceutically acceptable carrier or diluent. The composition may be formulated for treating a subject requiring or susceptible to requiring cognition enhancement, and packaged with instructions to treat a subject requiring or susceptible to requiring cognition enhancement.

The subject may be at risk requiring cognition enhancement, may be exhibiting symptoms of requiring cognition enhancement, may be susceptible to requiring cognition enhancement and/or may have been diagnosed with requiring cognition enhancement.

If the modulation of the status indicates that the subject may have a favorable clinical response to the treatment, the subject may be treated with the compound. For example, the subject can be administered therapeutically effective dose or doses of the compound.

Kits of the invention include kits for enhancing cognition in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. In aspects, the kits (and methods of using them) comprise instructions indicating that the compositions and/or treatment methods are contraindicated for (or not to be administered to) subjects that: (i) require and/or are taking CYP3A4, CYP 2B6-, or CYP 2D6-metabolized drugs; (ii) drink more than one alcoholic drink per day (e.g., 12-oz beer, 4-oz wine, etc).

Alternatively, the effects of compound of the invention can be characterized in vivo using animals models.

4. Pharmaceutical Compositions

The invention also provides a pharmaceutical composition, comprising an effective amount of a compound described herein and a pharmaceutically acceptable carrier. In a further embodiment, the effective amount is effective to treat a sexual disorder or hypoactive sexual desire disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral, buccal or sublingual administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound or composition herein.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

EXAMPLES

The invention is further illustrated by the following examples which are intended to illustrate but not limit the scope of the invention.

Materials

Small-Molecule Compounds— bupropion, trazodone, oxytocin, and testosterone (and their salt, solvates, hydrates, isomers, enantiomers, diastereomers, racemates; all of which are included herein) are available from commercial sources and/or readily synthesized using methods and reagents know in the art. Bupropion is also known as, i.e., β-Keto-3-chloro-N-tert-butylamphetamine, i.e., (±)-2-(tert-Butylamino)-1-(3-chlorophenyl)propan-1-one; trazodone is also known as, i.e., 2-{3-[4-(3-chlorophenyl)piperazin-1-yl]propyl}[1,2,4]triazolo[4,3-a]pyridin-3(2H)-one; oxytocin is also known as, i.e., 1-({(4R,7S,10S,13S,16S,19R)-19-amino-7-(2-amino-2-oxoethyl)-10-(3-amino-3-oxopropyl)-16-(4-hydroxybenzoyl)-13-[(1S)-1-methylpropyl]-6,9,12,15,18-pentaoxo-1,2-dithia-5,8,11,14,17-pentaazacycloicosan-4-yl}carbonyl)-L-prolyl-L-leucylglycinamide.

Example 1

Clinical Protocol— subjects in a single blind, sequential study are administered bupropion and trazodone in increasing dosages @ 3-4 weeks each, that is, from a 3 (or 4)-week placebo baseline, to an intermediate dose (@ another 3-4 weeks), to a maximum dose (@ a final 3-4 weeks). The subjects' feedback/reports on subjective (e.g., feelings, sensations, general response) and objective (e.g., response time, performance measures, partner response) is collated and analyzed against dosage. Each study also includes one or more patient(s) serving as a control (in demonstrating the synergistic effect between the two actives) would receive only bupropion, while the second and third will each be given a different fixed dose combination products having a defined ratio of active ingredients (e.g., bupropion and trazodone).

Example 2

Method.

A 36 year-old healthy male volunteer in a stable marital relationship for two years with no current sexual disorders, exposed himself sequentially to four treatments, each for 4 weeks: (1) Treatment B: Instant-release (IR) Bupropion (Bup) 150 mg in the morning and 100 mg in the evening; (2) Treatment T: IR trazodone (Trz) 50 mg t.i.d.; (3) Treatment $L_{low}$, IR Trz 25 mg b.i.d. plus IR Bup 150 mg in the morning and 100 mg in the evening; and (4) Treatment $L_{high}$, IR Trz 50 mg t.i.d. plus IR Bup 75 mg t.i.d. A washout of 1-4 weeks occurred between each treatment. Level and frequency of sexual desire was scored daily, as not improved (0), somewhat improved (1), or markedly improved (2). Sexual events were counted, and three domains (sexual arousal, orgasm, and overall satisfaction with the event) were scored. Each of the sexual event variables was converted to a simple patient's global impression of improvement (PGI; improved or not improved today compared to pre-treatment baseline). The 3 domains of sexual event improvements were summed for analysis. Bup is already recommended as a treatment for HSDD; Trz is not. Thus, Fisher's exact test was applied post-hoc to the PGIs for Treatment B vs. Treatment $L_{low}$ ($L_{10w}$) and vs. Treatment $L_{high}$ ($L_{high}$).

Results.

For sexual desire, the mean score with $L_{low}$ and $L_{high}$ was about twice that with Treatment B (two-tailed paired t-test, p<0.0001), and Treatment B was superior to Treatment T. For arousal, orgasm, and overall satisfaction with a sexual event, $L_{low}$ was associated with somewhat more improvements than with Treatment B in the third and fourth weeks of use. $L_{high}$ was associated with significantly more improvements than with Treatment B in the third and fourth weeks of use and in the total for all four weeks. Fisher's exact test, two-tailed, showed the combination of bupropion plus trazodone superior, p<0.05, for the 3-domain sum of sexual event improvement. This study conducted with the combination of bupropion plus trazodone showed increased benefits in sexual arousal, orgasm, and event satisfaction, after exposure for 4 weeks, compared to either bupropion alone or trazodone alone. The effects occurred at or below the target dosage of bupropion or trazodone in their current (antidepressant) labeling.

An independent researcher then scored the desire results as unimproved=0, somewhat improved=1, and markedly improved=2. Upon the advice of the independent researcher the subject dichotomized his sexual event results in a simple daily patient's global impression of improvement: improved or not improved today (compared to pre-treatment baseline). The independent researcher, when told that the results were positive for the subject but before seeing any of the data, decided to apply categorical tests to the most obvious comparisons between treatments: for the first two weeks, the second two weeks, and for all four weeks of treatment, low-dose combination of bupropion plus trazodone vs. corresponding dose of bupropion; and high-dose the combination of bupropion plus trazodone vs. same dose of trazodone. The test used for the desire score was a two-tailed paired t test, using all scores within a given treatment as repeated measures. The test used for the two-category variables was an online two-tailed Fisher's exact test using all scores within a given treatment as repeated measures. Both were from the website graphpad.com.*

*http://graphpad.com/quickcalcs/chisquared1.cfm

TABLE

Scores of desire, and counts of sexual event domain improved per treatment

| Treatment | 0-2 Daily Desire Score, total, % of max. (max. = 28), mean ± SD, p-value vs. Bup[1] | PGI Improved for Sexual Events, Sum of 3 domains[3] n/N, % improved | p-value vs. Bup[2] |
|---|---|---|---|
| Bup wks 1-2 | 9, 32% 0.65 ± 0.74 | 4/15, 27% | |
| Bup wks 3-4 | 14, 50% | 2/15, 13% | |
| Bup total | 0.82 ± 0.55 | 6/30, 20% | |
| wks 1-2 | 2, 7% 0.14 ± 0.53 p = 0.051 | 3/12, 25% | n.s. |
| Trz wks 3-4 | 0, 0% | 3/18, 17% | |
| Trz total | 2, 4% 0.07 ± 0.38 p < 0.0001 | 6/30, 20% | n.s. |
| $L_{low}$ wks 1-2 | 14, 50% 0.64 ± 0.74, n.s. | 3/15, 20% | n.s. |
| $L_{low}$ wks 3-4 | 28, 100% | 11/21, 52% | |
| $L_{low}$ total | 1.50 ± 0.88 P < 0.0001 | 14/36, 39% | n.s. |

TABLE-continued

Scores of desire, and counts of sexual event domain improved per treatment

| Treatment | 0-2 Daily Desire Score, total, % of max. (max. = 28), mean ± SD, p-value vs. Bup[1] | PGI Improved for Sexual Events, Sum of 3 domains[3] n/N, % improved | p-value vs. Bup[2] |
|---|---|---|---|
| $L_{high}$ wks 1-2 | 20, 71% 1.43 ± 0.94 p = 0.021 | 6/15, 40% | n.s. |
| $L_{high}$ wks 3-4 | 28, 100% | 13/18, 72% | |
| $L_{high}$ total | 1.71 ± 0.71, p < 0.0001 | 20/33, 61% | 0.0019 |

[1]P-values vs. corresponding treatment Bup, paired t test, two-tailed
[2]P-values vs. corresponding treatment Bup, two-tailed Fisher's exact test
[3]Sum of n improved in arousal, orgasm, and overall satisfaction
Note:
P-values larger than 0.1 are omitted from the table.
B or Bup is bupropion alone, T or Trz is trazodone alone, $L_{low}$ is the lower dose of Bup/Trz combination, $L_{high}$ is the higher dose of Bup/Trz combination.

For sexual desire, the response to T (Treatment T) was low, to B (Treatment B) was intermediate, and to $L_{low}$ and $L_{high}$ was sometimes strong in the first two weeks and uniformly strong (improvement rated as marked every day) in the second two weeks of treatment. The differences between each dose of L vs. B were highly statistically significant, p<0.0001.

B was markedly superior to T, p<0.05 for all comparisons.

For the sum of improvements in arousal, orgasm, and overall satisfaction with a sexual event, $L_{low}$ showed significantly more improvements than with B in the third and fourth weeks of use, 52% vs. 20%, p<0.05. $L_{high}$ was associated with significantly more improvements than with B in the third and fourth weeks of use (72% vs. 13%) and in the total for all four weeks (61% vs. 20%). Fisher's exact test, two-tailed, showed the combination of bupropion plus trazodone superior, p<0.05, for each of these 3-domain sums of sexual event improvement.

For improvements in orgasm or overall satisfaction for a sexual event, the numbers appeared too small and the numerical trends were generally too weak to show statistically significant differences. For arousal, however, $L_{high}$ was associated with significantly more improvements than with B in the third and fourth weeks of use (100% vs. 0%) and in the total for all four weeks (91% vs. 20%). Fisher's exact test, two-tailed, showed the combination of bupropion plus trazodone superior, p<0.05, for each of these 3-domain sums of sexual event improvement. A numerical trend also favored $L_{high}$ in weeks 1-2 by 4/5 vs. 2/5 (80% vs. 40%).

The applicability of these male results to female subjects with HSDD is possible given the similarities of desire dysfunction in men and women [Laumann 1999], and is to be tested next.

Example 3

Additional Study Design.
Further study is conducted as delineated in the Schematic below.

Schematic of Study Design

| | Week | | | | | |
|---|---|---|---|---|---|---|
| | 0 | 1 | 2 | 3 | 4 | 5 |
| Day | 1-7 | 8-15 | 15-21 | 22-29 | 29-35 | 36 |
| Period | Screening | First Dosing | Washout | Second Dosing | Washout | Final Evaluations |
| Group One | X | Low dose drug B + Low dose drug T | X | High dose drug B + High dose drug T | X | X |
| Group Two | X | High dose drug B | X | High dose drug T | X | X |

B or BUP = SR bupropion
T or TRZ = SR trazodone

Flow Chart of Study Data Collection

| | Period | | |
|---|---|---|---|
| | Screening | First and 8th day of each Treatment | Final Evaluation |
| Note: each subject undergoes 2 treatments, for 1 week each followed by a 1-week washout | Final Evaluation | | |
| Informed consent | X | | |
| FSFI-1 wk recall; FSDS-R-1 wk recall Both are self-rated (s) | X | X | X |
| Psychiatric history [clinician-rated (c)] | X | | |
| Relational/marital history (c) | X | | |
| PHQ-9 [self-rated (s)] | X | | |
| Beck Anxiety Inventory (s) | X | | |
| Sexual Interest and Desire Inventory - F (c) | X | | |
| Checklist for DSM-IV & DSM-5 female sexual disorders; FSD diagnoses (c) | X | | |
| Marital Adjustment Test (MAT) (s) | X | | X |
| Physical examination | X | | P.r.n. only |
| Laboratory analytes | X | | X |
| ECG, 12-lead | X | | X |
| Sexual Activity Log (s) | X | X | X |
| Sexual Desire Relationship Distress Scale (SDRDS) (s) if available from authors | X | X | X |
| Vital signs (supine and standing b.p., pulse)2 | X | Pre-dose & 1, 2, 4, 8 & 24 hr post-dose | X |
| AE inquiry and checklist2 | | | |
| Drug blood levels | | Pre-dose and 1, 2, 4, 6, 8, 12, 24 hr post-dose | |
| Cognitive test battery | | Pre-dose and 1, 2, and 4 hours post-dose | |
| Verbal Numeric Rating Scales of 6 feeling states (s) | X | | |
| Partner's tests (may do at home if use HTS) | IIEF MAT (p) SDRDS (p) | | IIEF MAT (p) SDRDS (p) |

Week 0: Informed consent, screening evaluations [Medical, psychiatric, social/relationship, and sexual history; diagnostics], measures of sexual dysfunction, and safety evaluations [physical examination, ECG, standard laboratory safety analytes]

Week 1: Treatment #1
Group 1
Low Dose combination of bupropion plus trazodone: 250 mg BUP+75 mg TRZ/day, given as 150 mg SR BUP in the morning and 100 mg SR BUP in the evening and 75 mg SR trazodone q.d.; and test battery. The test battery includes single-dose PK, steady-state PK and pharmacodynamics. Pharmacodynamics includes a cognitive test battery and numeric rating scales (NRS) of feeling states, which will be done in the morning of the first and last day of dosing, at pre-dose and at 1, 2, 4 and 8 hours post-dose. The cognitive testing battery includes choice reaction time, word recall, picture recognition, numeric and spatial working memory. The self-rated NRS of feeling states for sedation/activation includes drowsy, dizzy, nervous, agitated, and hyper. Cognitive testing will be done within −20 minutes before the hour; blood sampling will be done exactly on the hour; and VAS will be done within +15 minutes after the hour. Or
Group 2
150 mg SR BUP in the morning and 100 mg SR BUP in the evening
Week 2: washout #1
Week 3: Treatment #2:
Group 1
High Dose combination of bupropion plus trazodone (250 mg BUP+150 mg TRZ/day, given as 150 mg SR BUP in the morning and 100 mg SR BUP in the evening and 150 mg SR trazodone q.d.) and test battery or
Group 2
150 mg SR trazodone q.d.
Week 4: Washout #2

Example 4

Compositions of the invention can be made by combining the active agents (i.e., bupropion and trazodone) with one or more of the following excipients:
CARNAUBA WAX, CYSTEINE HYDROCHLORIDE, HYPROMELLOSES, MAGNESIUM STEARATE, CELLULOSE, MICROCRYSTALLINE, POLYETHYLENE, GLYCOL, POLYSORBATE 80, TITANIUM DIOXIDE, FD&C BLUE NO. 1;
Hydroxypropyl distarch phosphate (Contramid®), Hypromellose, Sodium stearyl fumarate, Colloidal silicon dioxide, Iron Oxide Yellow, Iron Oxide Red, Talc, Polyethylene Glycol 3350, Titanium Dioxide, Polyvinyl Alcohol, Black ink (food grade).

The disclosures of each and every patent, patent application and publication cited herein are hereby incorporated herein by reference in their entirety.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

Example 5

| Schematic of Study Design for a clinical trial of transnasal oxytocin | | | | | | | |
|---|---|---|---|---|---|---|---|
| Treatment Week | | | | | | | |
| | 0 | 1-4 | 5 | 6-9 | 10 | 11-14 | 14.1 |
| Day | 1-7[1] | 8-36 | 36-42 | 43-71 | 71-77 | 78-106 | 106[2] |
| Period | Screening | Control treatment | Washout #1 | Low-Dose oxytocin | Washout #2 | Moderate-Dose oxytocin | Final Evaluations |
| Dosing | None | Placebo | None | Oxytocin 12 IU/day | None | Oxytocin 24 IU/day | None |
| Alternative Dosing* | | | | Moderate-Dose Oxytocin 24 IU/day Oxytocin | | High Dose Oxytocin 40 IU/day oxytocin | |

[1]May shorten to 3 days if all screening requirements are met.
[2]Prolong to repeat any final evaluations needed because of clinical abnormalities.
*If efficacy and the maximum well tolerated dose are not found after 5-15 patients have been treated with the "Moderate Dose oxytocin," doses will be increased, and the "High Dose oxytocin" will be implemented for subsequent patients.

| Flow Chart | | | | | | | |
|---|---|---|---|---|---|---|---|
| | Screening[1] | Control (placebo) | | Low-dose OXYTOCIN | | Mod/High-dose OXYTOCIN | Final Visit[1] |
| Study Day | 1 | 8 | 36 | 43 | 71 | 78 | 106 | 106 |
| Informed consent | X | | | | | | | |
| Psychiatric history [c][2] | X | | | | | | | |
| Relational/marital history (c) | X | | | | | | | |
| PHQ-9[3] [self-rated (s)][4] | X | | | | | | | X |
| C-SSRS Screen Version[5] (c) | X | | | | | | | X |
| FSFI[6] with 4-week recall (s) | X | | | | | | | |
| FSFI with 1-week recall (s) | | X | X | X | X | X | X | |
| FSDS-R[7] w/30-day recall (s) | X | | | | | | | |
| FSDS-R with 7-day recall | | X | X | X | X | X | X | |
| FSFI-6[6] with 1-wk recall (s) FSDS-R[7] item 13 (s) | | Via web on days 15, 22, 29 | | Via web on days 50, 57, 64 | | Via web on days 85, 92, 99 | | |
| Pt's Global Impression of Improvement (s) | | Via web on d 15, 22, 29, 36 | | Via web on d 50, 57, 64, 71 | | Via web on d 85, 92, 99, 106 | | |
| Sexual function interview, Checklist for DSM-IV FSD diagnoses[8] (c) | X | | | | | | | |
| Marital Adjustment Test (s) | X | | | | | | | |
| Physical, pelvic examinations[9], Pap test (c) | Prn | | | | | | | Prn |
| Dosing | None | Start | End | Start | End | Start | End | |
| Supine & standing b.p., pulse[10] | X | XX | X | XX | X | XX | X | X |

| Flow Chart | | | | | |
|---|---|---|---|---|---|
| | Screening[1] | Control (placebo) | Low-dose OXYTOCIN | Mod/High-dose OXYTOCIN | Final Visit[1] |
| AE inquiry & checklist[11] (s, c) | X | XX      X | XX      X | XX      X | |
| CBC, ALT, AST (others prn[12]) | X | | | | X |

[1]Treatments may start any day of the week, provided the first day's dose is taken in the clinic. Each dosing period must last 28 days (1st and 29th day clinic visits are on same day of week).
[2]C = clinician-rated
[3]PHQ-9 = Patient Health questionnaire, 9-item depression module
[4]S = Self-rated by female subject
[5]C-SSRS = Columbia Suicide Severity Rating Scale, 6-item Screening/Triage version
[6]FSFI = Female Sexual Function Inventory. FSFI-6 = 6-item version of the FSFI
[7]FSDS-R = Female Sexual Distress Scale - Revised.
[8]Each DSM-IV-TR sexual symptom to be rated as present or not, and causing distress or not.
[9]To be performed as needed to investigate any symptoms that began within the prior 3 months.
[10]On the first day of each treatment, supine and standing BP and pulse pre-dose and 3:30 hours post-dose, and p.r.n. palpitations, faintness, or other CV-referable symptoms.
[11]On the first day of each treatment, AE general inquiry and 16-item Side Effects Checklist pre-dose and 3:50 hours post-dose. Patient completes form; clinician checks it to confirm type and severity of AE..
[12]If new findings occur & persist until the final visit, perform relevant laboratory analytes.

Example 6

Schematic of Study Design for a clinical trial of oxytocin plus bupropion

| | Treatment Week | | | | | | |
|---|---|---|---|---|---|---|---|
| | 0 | 1-4 | 5 | 6-9 | 10 | 11-14 | 14.1 |
| Day | 1-7[1] | 8-36 | 36-42 | 43-71 | 71-77 | 78-106 | 106[2] |
| Period | Screening | Control treatment | Washout #1 | Low-Dose OXYTOCIN | Washout #2 | Moderate-Dose OXYTOCIN* | Final Evaluations |
| Dosing | None | BUP[3] 150 mg q.a.m. and increasing on day 4 to 150 mg b.i.d. | None | BUP 150 mg q.d plus OT[4] 12 IU q.d.* | None | BUP 150 mg b.i.d. and OT 24 IU b.i.d.* | None |
| Alternative Dosing* | | | | Moderate-Dose Oxytocin BUP 150 mg b.i.d. and OT 24 IU b.i.d.* | | High-Dose Oxytocin BUP 200 mg b.i.d. and OT 40 IU b.i.d.* | |

[3]May shorten to 3 days if all screening requirements are met.
[4]Prolong to repeat any final evaluations needed because of clinical abnormalities.
5. BUP = SR bupropion
6. OT = oxytocin
*If efficacy and the maximum well tolerated dose are not found after 5-15 patients have been treated with the "Moderate Dose Oxytocin," doses will be increased, and the "High Dose Oxytocin" will be implemented for subsequent patients.

| Flow Chart | | | | | | | |
|---|---|---|---|---|---|---|---|
| | Screening[1] | Control (BUP)[1] | | Lower-dose OT + BUP | | Higher-dose OT + BUP | Final Visit[1] |
| Study Day | 1 | 8 | 36 | 43 | 71 | 78      106 | 106 |
| Informed consent | X | | | | | | |
| Psychiatric history [c][2] | X | | | | | | |
| Relational/marital history (c) | X | | | | | | |
| PHQ-9[3] [self-rated (s)][4] | X | | | | | | X |
| C-SSRS Screen Version[5] (c) | X | | | | | | X |
| FSFI[6] with 4-week recall (s) | X | | | | | | |
| FSFI with 1-week recall (s) | | X | X | X | X | X      X | |
| FSDS-R[7] w/30-day recall (s) | X | | | | | | |
| FSDS-R with 7-day recall | | X | X | X | X | X      X | |
| FSFI-6[6] with 1-wk recall (s) | | Via web on days 15, 22, 29 | | Via web on days 50, 57, 64 | | Via web on days 85, 92, 99 | |
| FSDS-R[7] item 13 (s) | | | | | | | |
| Pt's Global Impression of Improvement (s) | | Via web on d 15, 22, 29, 36 | | Via web on d 50, 57, 64, 71 | | Via web on d 85, 92, 99, 106 | |

| | Screening[1] | Control (BUP)[1] | | Lower-dose OT + BUP | | Higher-dose OT + BUP | | Final Visit[1] |
|---|---|---|---|---|---|---|---|---|
| | | Flow Chart | | | | | | |
| Sexual function interview, Checklist for DSM-IV FSD diagnoses[8] (c) | X | | | | | | | |
| Marital Adjustment Test (s) | X | | | | | | | |
| Physical, pelvic examinations[9], Pap test (c) | Prn | | | | | | | Prn |
| Dosing | None | Start | End | Start | End | Start | End | |
| Supine & standing b.p., pulse[10] | X | XX | X | XX | X | XX | X | X |
| AE inquiry & checklist[11] (s, c) | X | XX | X | XX | X | XX | X | X |
| CBC, ALT, AST (others prn[12]) | X | | | | | | | X |

[1]Treatments may start any day of the week, provided the first day's dose is taken in the clinic. Each dosing period must last 28 days (1st and 29th day clinic visits are on same day of week).
[2]C = clinician-rated
[3]PHQ-9 = Patient Health questionnaire, 9-item depression module
[4]S = Self-rated by female subject
[5]C-SSRS = Columbia Suicide Severity Rating Scale, 6-item Screening/Triage version
[6]FSFI = Female Sexual Function Inventory. FSFI-6 = 6-item version of the FSFI
[7]FSDS-R = Female Sexual Distress Scale - Revised.
[8]Each sexual symptom in DSM-IV-TR to be rated as present or not, causing distress or not.
[9]To be performed as needed to investigate any symptoms that began within the prior 3 months.
[10]On the first day of each treatment, supine and standing BP and pulse pre-dose and 3:30 hours post-dose, and p.r.n. palpitations, faintness, or other CV-referable symptoms.
[11]On the first day of each treatment, AE general inquiry and 16-item Side Effects Checklist pre-dose and 3:50 hours post-dose. Patient completes form; clinician checks it to confirm type and severity of AE.
[12]If new findings occur & persist until the final visit, perform relevant laboratory analytes.

Example 7

Schematic of Study Design for a clinical trial of oxytocin (OT) and sustained release (SR) trazodone (TRZ)

| Treatment Week | 0 | 1-4 | 5 | 6-9 | 10 | 11-14 | 14.1 |
|---|---|---|---|---|---|---|---|
| Day | 1-7[1] | 8-36 | 36-42 | 43-71 | 71-77 | 78-106 | 106[2] |
| Period | Screening | Control treatment | Washout #1 | Low-Dose OT + TRZ | Washout #2 | Moderate-Dose OT + TRZ* | Final Evaluations |
| Dosing | None | SR TRZ[3] 150 mg q.a.m. and increasing on day 4 to 150 mg b.i.d. | None | OT 12 IU q.d. plus TRZ[4] 75 mg q.d* | None | OT 12 IU b.i.d. and TRZ 75 mg b.i.d.* | None |
| Alternative Dosing* | | | | Moderate-Dose OT + TRZ OT 12 IU b.i.d. and TRZ 75 mg b.i.d.* | | High-Dose OT + TRZ OT 40 IU q.d. and TRZ 150 mg b.i.d.* | |

[1]May shorten to 3 days if all screening requirements are met.
[2]Prolong to repeat any final evaluations needed because of clinical abnormalities.
[3]OT = transnasal or SR oral oxytocin
[4]TRZ = SR trazodone
*If efficacy and the maximum well tolerated dose are not found after 5-15 patients have been treated with the "Moderate Dose OT + TRZ," doses will be increased, and a "High Dose OT + TRZ" of 40 IU OT and 150 mg TRZ b.i.d. will be implemented for subsequent patients.

| | Screening[1] | Control (BUP)[1] | Lower-dose OT + TRZ[1] | Higher-dose OT + TRZ[1] | Final Visit[1] |
|---|---|---|---|---|---|
| | | Flow Chart | | | |
| Study Day | 1 | 8  36 | 43  71 | 78  106 | 106 |
| Informed consent | X | | | | |
| Psychiatric history [c][2] | X | | | | |
| Relational/marital history (c) | X | | | | |
| PHQ-9[3] [self-rated (s)][4] | X | | | | X |
| C-SSRS Screen Version[5] (c) | X | | | | X |

-continued

| | Screening[1] | Control (BUP)[1] | | Lower-dose OT + TRZ[1] | | Higher-dose OT + TRZ[1] | | Final Visit[1] |
|---|---|---|---|---|---|---|---|---|
| Flow Chart | | | | | | | | |
| FSFI[6] with 4-week recall (s) | X | | | | | | | |
| FSFI with 1-week recall (s) | | X | X | X | X | X | X | |
| FSDS-R[7] w/30-day recall (s) | X | | | | | | | |
| FSDS-R with 7-day recall | | X | X | X | X | X | X | |
| FSFI-6[6] with 1-wk recall (s) | | Via web on | | Via web on | | Via web on | | |
| FSDS-R[7] item 13 (s) | | days 15, 22, 29 | | days 50, 57, 64 | | days 85, 92, 99 | | |
| Pt's Global Impression of | | Via web on | | Via web on | | Via web on | | |
| Improvement (s) | | d 15, 22, 29, 36 | | d 50, 57, 64, 71 | | d 85, 92, 99, 106 | | |
| Sexual function interview, Checklist for DSM-IV FSD diagnoses[8] (c) | X | | | | | | | |
| Marital Adjustment Test (s) | X | | | | | | | |
| Physical, pelvic examinations[9], Pap test (c) | Prn | | | | | | | Prn |
| Dosing | None | Start | End | Start | End | Start | End | |
| Supine & standing b.p., pulse[10] | X | XX | X | XX | X | XX | X | X |
| AE inquiry & checklist[11] (s, c) | X | XX | X | XX | X | XX | X | |
| CBC, ALT, AST (others prn[12]) | X | | | | | | | X |

[1]Treatments may start any day of the week, provided the first day's dose is taken in the clinic. Each dosing period must last 28 days (1st and 29th day clinic visits are on same day of week).
[2]C = clinician-rated
[3]PHQ-9 = Patient Health questionnaire, 9-item depression module
[4]S = Self-rated by female subject
[5]C-SSRS = Columbia Suicide Severity Rating Scale, 6-item Screening/Triage version
[6]FSFI = Female Sexual Function Inventory. FSFI-6 = 6-item version of the FSFI
[7]FSDS-R = Female Sexual Distress Scale - Revised.
[8]Each symptom as in the DSM-IV-TR, to be rated as present or not, causing distress or not.
[9]To be performed as needed to investigate any symptoms that began within the prior 3 months.
[10]On the first day of each treatment, supine and standing BP and pulse pre-dose and 3:30 hours post-dose, and p.r.n. palpitations, faintness, or other CV-referable symptoms.
[11]On the first day of each treatment, AE general inquiry and 16-item Side Effects Checklist pre-dose and 3:50 hours post-dose. Patient completes form; clinician checks it to confirm type and severity of AE.
[12]If new findings occur & persist until the final visit, perform relevant laboratory analytes.

Example 8

Schematic of Study Design for a clinical trial of oxytocin (OT), bupropion (BUP or B), and trazodone (TRZ or T)

| | Treatment Week | | | | | | |
|---|---|---|---|---|---|---|---|
| | 0 | 1-4 | 5 | 6-9 | 10 | 11-14 | 14.1 |
| Day | 1-7[1] | 8-36 | 36-42 | 43-71 | 71-77 | 78-106 | 106[2] |
| Period | Screening | Control treatment | Washout #1 | Low-Dose OT + B + T | Washout #2 | Moderate-Dose OT + B + T* | Final Evaluations |
| Dosing | None | BUP[3] 150 mg q.a.m. and increasing on day 4 to 150 mg b.i.d. | None | BUP 150 mg q.d. + 12 IU OT + TRZ[4] 75 mg q.d.* | None | BUP 150 mg b.i.d. + 12 IU Ot + TRZ 75 mg b.i.d.* | None |
| Alternative Dosing* | | | | Moderate-Dose OT + B + T BUP 150 mg b.i.d._24 IU OT + TRZ 75 mg b.i.d.* | | High-dose OT + B + T BUP 200 mg b.i.d. + 40 IU OT + TRZ 150 mg b.i.d.* | |

[1]May shorten to 3 days if all screening requirements are met.
[2]Prolong to repeat any final evaluations needed because of clinical abnormalities
[3]BLIP = SR bupropion
[4]TRZ = SR trazodone
*If efficacy and the maximum well tolerated dose are not found after 5-15 patients have been treated with the "Moderate Dose OT + B + T," doses will be increased, and a "High Dose OT + B + T" will be implemented for subsequent patients.

| | Screening[1] | Control (BUP)[1] | | Low-dose OT + B + T[1] | | Mod/High-dose OT + B + T[1] | | Final Visit[1] |
|---|---|---|---|---|---|---|---|---|
| Study Day | 1 | 8 | 36 | 43 | 71 | 78 | 106 | 106 |
| Informed consent | X | | | | | | | |
| Psychiatric history [c][2] | X | | | | | | | |
| Relational/marital history (c) | X | | | | | | | |
| PHQ-9[3] [self-rated (s)][4] | X | | | | | | | X |
| C-SSRS Screen Version[5] (c) | X | | | | | | | X |
| FSFI[6] with 4-week recall (s) | X | | | | | | | |
| FSFI with 1-week recall (s) | | X | X | X | X | X | X | |
| FSDS-R[7] w/30-day recall (s) | X | | | | | | | |
| FSDS-R with 7-day recall | | X | X | X | X | X | X | |
| FSFI-6[6] with 1-wk recall (s) FSDS-R[7] item 13 (s) | | Via web on days 15, 22, 29 | | Via web on days 50, 57, 64 | | Via web on days 85, 92, 99 | | |
| Pt's Global Impression of Improvement (s) | | Via web on d 15, 22, 29, 36 | | Via web on d 50, 57, 64, 71 | | Via web on d 85, 92, 99, 106 | | |
| Sexual function interview, Checklist for DSM-IV FSD diagnoses[8] (c) | X | | | | | | | |
| Marital Adjustment Test (s) | X | | | | | | | |
| Physical, pelvic examinations[9], Pap test (c) | Prn | | | | | | | Prn |
| Dosing | None | Start | End | Start | End | Start | End | |
| Supine & standing b.p., pulse[10] | X | XX | X | XX | X | XX | X | X |
| AE inquiry & checklist[11] (s, c) | X | XX | X | XX | X | XX | X | |
| CBC, ALT, AST (others prn[12]) | X | | | | | | | X |

[1]Treatments may start any day of the week, provided the first day's dose is taken in the clinic. Each dosing period must last 28 days (1st and 29th day clinic visits are on same day of week).
[2]C = clinician-rated
[3]PHQ-9 = Patient Health questionnaire, 9-item depression module
[4]S = Self-rated by female subject
[5]C-SSRS = Columbia Suicide Severity Rating Scale, 6-item Screening/Triage version
[6]FSFI = Female Sexual Function Inventory. FSFI-6 = 6-item version of the FSFI
[7]FSDS-R = Female Sexual Distress Scale - Revised.
[8]The 16 most common AE with either BUP or TRZ as in US labeling of these drugs, plus sexual desire and sexual arousal.
[9]To be performed as needed to investigate any symptoms that began within the prior 3 months.
[10]On the first day of each treatment, supine and standing BP and pulse pre-dose and 3:30 hours post-dose, and p.r.n. palpitations, faintness, or other CV-referable symptoms.
[11]On the first day of each treatment, AE general inquiry and 16-item Side Effects Checklist pre-dose and 3:50 hours post-dose. Patient completes form; clinician checks it to confirm type and severity of AE. See Appendix H.
[12]If new findings occur & persist until the final visit, perform relevant laboratory analytes.

What is claimed is:

1. A composition comprising a 5-HT$_{2A}$ antagonist, a norepinephrine-dopamine reuptake inhibitor, an oxytocin receptor (OXTR) agonist, and a pharmaceutically acceptable carrier.

2. The composition of claim 1, wherein the 5-HT$_{2A}$ antagonist is also a 5-HT$_{1A}$ receptor agonist.

3. The composition of claim 1, comprising trazodone, bupropion, and oxytocin.

4. The composition of claim 1, comprising bupropion in a dosage range of 200-450 mg.

5. The composition of claim 1, comprising trazodone in a dosage range of 25-450 mg.

6. The composition of claim 1, comprising oxytocin in a dosage range of 4-400 International Units.

7. The composition of claim 1, comprising trazodone in a dosage range of 1-450 mg, bupropion in a dosage range of 1-450 mg, and oxytocin in a dosage range of 4-400 International Units.

8. A method of making a composition comprising combining a 5-HT$_{1A}$ agonist, a 5-HT$_{2A}$ antagonist, a norepinephrine-dopamine reuptake inhibitor, an oxytocin receptor (OXTR) agonist, and a pharmaceutically acceptable carrier.

9. The method of claim 8, comprising combining bupropion, trazodone, oxytocin, and a pharmaceutically acceptable carrier.

10. A method of treating a sexual disorder in a subject comprising administering to the subject a composition according to claim 1.

11. The method of claim 10, wherein the sexual disorder is hypoactive sexual desire disorder (HSDD).

12. The method of claim 10, wherein the sexual disorder is female orgasm disorder (FOD).

13. The method of claim 10, wherein the sexual disorder is female sexual arousal disorder (FSAD).

14. The method of claim 10, wherein the sexual disorder is sexual pain dysfunction.

15. The method of claim 10, wherein the sexual disorder is male HSDD.

16. A method of treating a cognitive disorder in a subject comprising administering to the subject a composition according to claim 1.

17. The method in claim 16, wherein the cognitive disorder is dementia.

18. The method in claim 17, wherein the dementia is Alzheimer's disease, frontotemporal lobar degeneration, dementia with Lewy bodies, Parkinson's disease, Huntington's disease, multi-infarct dementia, dementia resulting from infections affecting the central nervous system, dementia resulting from chronic drug use, dementia resulting from hydrocephalus, dementia resulting from brain injury, or dementia resulting from a brain tumor.

19. The method in claim 16, wherein the cognitive disorder is cognitive disability.

20. The method in claim 19, wherein the cognitive disability is schizophrenia, schizoaffective disorder, bipolar disorder, or major depression.

* * * * *